United States Patent
Dantus et al.

(10) Patent No.: US 8,618,470 B2
(45) Date of Patent: Dec. 31, 2013

(54) LASER BASED IDENTIFICATION OF MOLECULAR CHARACTERISTICS

(75) Inventors: Marcos Dantus, Okemos, MI (US); Vadim V. Lozovoy, Holt, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1176 days.

(21) Appl. No.: 12/085,878

(22) PCT Filed: Nov. 29, 2006

(86) PCT No.: PCT/US2006/045686
§ 371 (c)(1), (2), (4) Date: Jun. 17, 2009

(87) PCT Pub. No.: WO2007/064703
PCT Pub. Date: Jun. 7, 2007

(65) Prior Publication Data
US 2009/0296744 A1    Dec. 3, 2009

Related U.S. Application Data

(60) Provisional application No. 60/740,898, filed on Nov. 30, 2005.

(51) Int. Cl.
*G01D 18/00*     (2006.01)
(52) U.S. Cl.
USPC ........................................... 250/252.1
(58) Field of Classification Search
USPC ............................................ 250/252.1
See application file for complete search history.

(56) References Cited

U.S. PATENT DOCUMENTS

| | | |
|---|---|---|
| 3,214,563 A | 10/1965 | Ford |
| 3,611,182 A | 10/1971 | Treacy |
| 3,919,881 A | 11/1975 | Metherell |
| 3,988,704 A | 10/1976 | Rice et al. |
| 4,167,662 A | 9/1979 | Steen |
| 4,288,691 A | 9/1981 | Horton |
| 4,394,780 A | 7/1983 | Mooradian |
| 4,477,905 A | 10/1984 | Sweeney |
| 4,512,660 A | 4/1985 | Goldberg |
| 4,616,333 A | 10/1986 | Shimoni et al. |

(Continued)

FOREIGN PATENT DOCUMENTS

| | | |
|---|---|---|
| EP | 0 605 110 | 7/1994 |
| EP | 0842729 A1 | 5/1998 |

(Continued)

OTHER PUBLICATIONS

Kawasaki et al., Enantioselective Synthesis of Near Enantiopure Compound by Asymmetric Autocatalysis Triggered by Asymmetric Photolysis with Circularly Polarized Light, Feb. 16, 2005, J.Am. Chem.Soc., vol. 127, pp. 3274-3275.*

(Continued)

*Primary Examiner* — Christine Sung
(74) *Attorney, Agent, or Firm* — Harness, Dickey & Pierce, P.L.C.

(57) ABSTRACT

Enantiomers are characterized, identified, synthesized and/or modified with a shaped laser pulse. In another aspect of the present invention, binary shaping and circular polarization are employed with a laser pulse. A further aspect of the present invention provides a quarter-wave plate in combination with one or more pulse shapers.

27 Claims, 4 Drawing Sheets

(56) References Cited

U.S. PATENT DOCUMENTS

| | | |
|---|---|---|
| 4,621,006 A | 11/1986 | Terry et al. |
| 4,655,547 A | 4/1987 | Heritage et al. |
| 4,746,193 A | 5/1988 | Heritage et al. |
| 4,772,854 A | 9/1988 | Silberberg |
| 4,812,776 A | 3/1989 | Sasaki |
| 4,819,239 A | 4/1989 | Sharp et al. |
| 4,834,474 A | 5/1989 | George et al. |
| 4,853,065 A | 8/1989 | Terry et al. |
| 4,856,860 A | 8/1989 | Silberberg et al. |
| 4,866,699 A | 9/1989 | Brackett et al. |
| 4,896,547 A | 1/1990 | Arney et al. |
| 4,913,934 A | 4/1990 | Sharp et al. |
| 4,928,316 A | 5/1990 | Heritage et al. |
| 4,999,840 A | 3/1991 | Negus |
| 5,021,282 A | 6/1991 | Terry et al. |
| 5,034,613 A | 7/1991 | Denk |
| 5,048,029 A | 9/1991 | Skupsky et al. |
| 5,054,027 A | 10/1991 | Goodberlet et al. |
| 5,077,619 A | 12/1991 | Toms |
| 5,095,487 A | 3/1992 | Meyerhofer et al. |
| 5,130,994 A | 7/1992 | Madey et al. |
| 5,132,512 A | 7/1992 | Sanders et al. |
| 5,132,824 A | 7/1992 | Patel et al. |
| 5,154,963 A | 10/1992 | Terry |
| 5,166,818 A | 11/1992 | Chase et al. |
| 5,235,606 A | 8/1993 | Mourou et al. |
| 5,239,607 A | 8/1993 | da Silva et al. |
| 5,311,873 A | 5/1994 | Savard et al. |
| 5,341,236 A | 8/1994 | Stappaerts |
| 5,349,591 A | 9/1994 | Weston et al. |
| 5,359,410 A | 10/1994 | Diels et al. |
| 5,391,199 A | 2/1995 | Ben-Haim |
| 5,400,350 A | 3/1995 | Galvanauskas |
| 5,406,408 A | 4/1995 | Ellingson et al. |
| 5,414,540 A | 5/1995 | Patel et al. |
| 5,414,541 A | 5/1995 | Patel et al. |
| 5,443,489 A | 8/1995 | Ben-Haim |
| 5,450,846 A | 9/1995 | Goldreyer |
| 5,463,200 A | 10/1995 | James et al. |
| 5,485,849 A | 1/1996 | Panescu et al. |
| 5,526,155 A | 6/1996 | Knox et al. |
| 5,526,171 A | 6/1996 | Warren |
| 5,530,544 A | 6/1996 | Trebino et al. |
| 5,541,947 A | 7/1996 | Mourou et al. |
| 5,572,355 A | 11/1996 | Cotton et al. |
| 5,585,913 A | 12/1996 | Hariharan et al. |
| 5,589,955 A | 12/1996 | Amako et al. |
| 5,615,673 A | 4/1997 | Berger et al. |
| 5,631,758 A | 5/1997 | Knox et al. |
| 5,633,885 A | 5/1997 | Galvanauskas et al. |
| 5,636,050 A | 6/1997 | Alfano et al. |
| 5,637,966 A | 6/1997 | Umstadter et al. |
| 5,682,262 A | 10/1997 | Wefers et al. |
| 5,684,595 A | 11/1997 | Kato et al. |
| 5,689,361 A | 11/1997 | Damen et al. |
| 5,704,700 A | 1/1998 | Kappel et al. |
| 5,719,650 A | 2/1998 | Wefers et al. |
| 5,726,855 A | 3/1998 | Mourou et al. |
| 5,734,503 A | 3/1998 | Szipocs et al. |
| 5,754,292 A | 5/1998 | Kane et al. |
| 5,759,767 A | 6/1998 | Lakowicz |
| 5,774,213 A | 6/1998 | Trebino et al. |
| 5,793,091 A | 8/1998 | Devoe |
| 5,798,867 A | 8/1998 | Uchida et al. |
| 5,822,097 A | 10/1998 | Tournois |
| 5,828,459 A | 10/1998 | Silberberg |
| 5,832,013 A | 11/1998 | Yessik et al. |
| 5,854,431 A | 12/1998 | Linker et al. |
| 5,862,287 A | 1/1999 | Stock et al. |
| 5,867,304 A | 2/1999 | Galvanauskas et al. |
| 5,883,309 A | 3/1999 | Vossiek et al. |
| 5,898,373 A | 4/1999 | Murad et al. |
| 5,915,268 A | 6/1999 | Linker et al. |
| 5,936,732 A | 8/1999 | Smirl et al. |
| 5,956,173 A | 9/1999 | Svelto et al. |
| 5,956,354 A | 9/1999 | Yan |
| 5,994,687 A | 11/1999 | Chanteloup et al. |
| 6,002,480 A | 12/1999 | Izatt et al. |
| 6,008,899 A | 12/1999 | Trebino et al. |
| 6,042,603 A | 3/2000 | Fisher et al. |
| 6,057,919 A | 5/2000 | Machida et al. |
| 6,058,132 A | 5/2000 | Iso et al. |
| 6,072,813 A | 6/2000 | Tournois |
| 6,080,148 A | 6/2000 | Damasco et al. |
| 6,081,543 A | 6/2000 | Liu et al. |
| 6,111,251 A | 8/2000 | Hillenkamp |
| 6,122,419 A | 9/2000 | Kurokawa et al. |
| 6,130,426 A | 10/2000 | Laukien et al. |
| 6,156,527 A | 12/2000 | Schmidt et al. |
| 6,166,385 A | 12/2000 | Webb et al. |
| 6,178,041 B1 | 1/2001 | Simon |
| 6,181,463 B1 | 1/2001 | Galvanauskas et al. |
| 6,184,490 B1 | 2/2001 | Schweizer |
| 6,191,386 B1 | 2/2001 | Albright et al. |
| 6,198,568 B1 | 3/2001 | Galvanauskas et al. |
| 6,219,142 B1 | 4/2001 | Kane |
| 6,259,104 B1 | 7/2001 | Baer |
| 6,272,156 B1 | 8/2001 | Reed et al. |
| 6,288,782 B1 | 9/2001 | Worster |
| 6,295,860 B1 | 10/2001 | Sakairi et al. |
| 6,296,810 B1 | 10/2001 | Ulmer |
| 6,316,153 B1 | 11/2001 | Goodman |
| 6,327,068 B1 | 12/2001 | Silberberg et al. |
| 6,337,606 B1 | 1/2002 | Brombaugh et al. |
| 6,344,653 B1 | 2/2002 | Webb et al. |
| 6,375,697 B2 | 4/2002 | Davies |
| 6,391,229 B1 | 5/2002 | Watanabe et al. |
| 6,396,856 B1 | 5/2002 | Sucha et al. |
| 6,402,898 B1 * | 6/2002 | Brumer et al. ........... 204/157.61 |
| 6,421,154 B1 | 7/2002 | Diels et al. |
| 6,479,822 B1 | 11/2002 | Nelson et al. |
| 6,480,656 B1 | 11/2002 | Islam et al. |
| 6,498,801 B1 | 12/2002 | Dudelzak et al. |
| 6,504,612 B2 | 1/2003 | Trebino |
| 6,515,257 B1 | 2/2003 | Jain et al. |
| 6,566,667 B1 | 5/2003 | Partlo et al. |
| 6,573,493 B1 | 6/2003 | Futami et al. |
| 6,577,782 B1 | 6/2003 | Leaird et al. |
| 6,603,600 B2 | 8/2003 | Pang |
| 6,610,351 B2 | 8/2003 | Shchegolikhin et al. |
| 6,610,977 B2 | 8/2003 | Megerle |
| 6,621,613 B2 | 9/2003 | Silberberg et al. |
| 6,625,181 B1 | 9/2003 | Oshemkov et al. |
| 6,631,333 B1 | 10/2003 | Lewis et al. |
| 6,642,513 B1 | 11/2003 | Jenkins et al. |
| 6,678,450 B1 | 1/2004 | Franson |
| 6,684,682 B2 | 2/2004 | Stemmle et al. |
| 6,697,196 B2 | 2/2004 | Suzuki |
| 6,708,572 B2 | 3/2004 | Jenkins et al. |
| 6,723,991 B1 | 4/2004 | Sucha et al. |
| 6,753,957 B1 | 6/2004 | Graft et al. |
| 6,757,463 B2 | 6/2004 | Hutchinson et al. |
| 6,795,456 B2 | 9/2004 | Scaggs |
| 6,795,777 B1 | 9/2004 | Scully et al. |
| 6,801,318 B2 | 10/2004 | Fu et al. |
| 6,801,551 B1 | 10/2004 | Delfyett et al. |
| 6,804,000 B2 | 10/2004 | Roorda et al. |
| 6,804,045 B2 | 10/2004 | Barty |
| 6,857,744 B2 | 2/2005 | Nakada et al. |
| 6,879,426 B1 | 4/2005 | Weiner |
| 6,885,325 B2 | 4/2005 | Omelyanchouk et al. |
| 6,885,683 B2 | 4/2005 | Fermann et al. |
| 6,914,668 B2 | 7/2005 | Brestel et al. |
| 6,915,040 B2 | 7/2005 | Willner et al. |
| 6,917,631 B2 | 7/2005 | Richardson et al. |
| 6,930,779 B2 | 8/2005 | McGrew |
| 6,963,591 B2 | 11/2005 | Tulloch et al. |
| 7,033,519 B2 | 4/2006 | Taylor et al. |
| 7,049,543 B2 | 5/2006 | Roos et al. |
| 7,057,788 B2 | 6/2006 | Ohbayashi et al. |
| 7,088,435 B2 | 8/2006 | Brestel et al. |
| 7,096,125 B2 | 8/2006 | Padmanabhan et al. |
| 7,105,811 B2 | 9/2006 | Dantus et al. |
| 7,113,327 B2 | 9/2006 | Gu et al. |

(56) References Cited

U.S. PATENT DOCUMENTS

| | | |
|---|---|---|
| 7,132,223 B2 | 11/2006 | Schroeder et al. |
| 7,169,709 B2 | 1/2007 | Koide |
| 7,170,030 B2 | 1/2007 | Haight et al. |
| 7,170,598 B2 | 1/2007 | Walla et al. |
| 7,224,518 B2 | 5/2007 | Tauser et al. |
| 7,256,885 B2 | 8/2007 | Silberberg et al. |
| 7,276,103 B2 | 10/2007 | Wöste et al. |
| 7,289,203 B2 | 10/2007 | Frankel |
| 7,342,223 B2 | 3/2008 | Ohkubo et al. |
| 7,348,569 B2 | 3/2008 | Feurer et al. |
| 7,369,773 B2 | 5/2008 | Weiner |
| 7,391,557 B1 | 6/2008 | Bruch et al. |
| 7,403,281 B2 | 7/2008 | Carron et al. |
| 7,403,282 B2 | 7/2008 | Silberberg et al. |
| 7,411,166 B2 | 8/2008 | Wolleschensky et al. |
| 7,439,497 B2 | 10/2008 | Dantus et al. |
| 7,450,618 B2 | 11/2008 | Dantus |
| 7,474,467 B2 | 1/2009 | Trebino |
| 7,567,596 B2 | 7/2009 | Dantus et al. |
| 7,576,907 B1 | 8/2009 | Bartels et al. |
| 7,583,710 B2 | 9/2009 | Dantus et al. |
| 7,609,731 B2 | 10/2009 | Dantus et al. |
| 7,826,051 B2 | 11/2010 | Silberberg et al. |
| 7,973,936 B2 | 7/2011 | Dantus |
| 7,989,731 B2 | 8/2011 | Bischoff et al. |
| 8,208,504 B2 | 6/2012 | Dantus et al. |
| 8,208,505 B2 | 6/2012 | Dantus et al. |
| 8,265,110 B2 | 9/2012 | Dantus et al. |
| 8,300,669 B2 | 10/2012 | Dantus et al. |
| 8,311,069 B2 | 11/2012 | Dantus et al. |
| 2001/0015411 A1 | 8/2001 | Ohdaira et al. |
| 2001/0015990 A1 | 8/2001 | Miyai |
| 2001/0017727 A1 | 8/2001 | Sucha et al. |
| 2002/0025490 A1 | 2/2002 | Shchegolikhin et al. |
| 2002/0086245 A1 | 7/2002 | Zait et al. |
| 2002/0093653 A1 | 7/2002 | Detalle et al. |
| 2002/0097761 A1 | 7/2002 | Sucha et al. |
| 2002/0176809 A1 | 11/2002 | Siess |
| 2003/0063884 A1 | 4/2003 | Smith et al. |
| 2003/0099264 A1 | 5/2003 | Dantus et al. |
| 2003/0123051 A1 | 7/2003 | McGrew |
| 2003/0194165 A1 | 10/2003 | Silberberg et al. |
| 2003/0210400 A1 | 11/2003 | Joffre et al. |
| 2004/0012837 A1 | 1/2004 | Kaplan et al. |
| 2004/0021243 A1 | 2/2004 | Shih et al. |
| 2004/0031906 A1 | 2/2004 | Glecker |
| 2004/0043443 A1 | 3/2004 | Lejeune |
| 2004/0058058 A1 | 3/2004 | Shchegolikhin et al. |
| 2004/0089804 A1 | 5/2004 | Dantus et al. |
| 2004/0128081 A1 | 7/2004 | Rabitz et al. |
| 2004/0145735 A1 | 7/2004 | Silberberg et al. |
| 2004/0155184 A1 | 8/2004 | Stockman et al. |
| 2004/0189990 A1 | 9/2004 | Shilling |
| 2004/0233944 A1 | 11/2004 | Dantus et al. |
| 2004/0240037 A1 | 12/2004 | Harter |
| 2004/0259234 A1 | 12/2004 | Chou et al. |
| 2004/0263950 A1 | 12/2004 | Fermann et al. |
| 2005/0017160 A1 | 1/2005 | Wolleschensky et al. |
| 2005/0021243 A1 | 1/2005 | Dantus et al. |
| 2005/0036202 A1 | 2/2005 | Cohen et al. |
| 2005/0103759 A1 | 5/2005 | Li et al. |
| 2005/0117864 A1* | 6/2005 | Dziekan et al. ............... 385/125 |
| 2005/0134687 A1* | 6/2005 | Kaminsky et al. ............. 348/169 |
| 2005/0155958 A1 | 7/2005 | Arai et al. |
| 2005/0161669 A1 | 7/2005 | Jovanovich et al. |
| 2005/0185188 A1 | 8/2005 | McGrew |
| 2005/0226287 A1 | 10/2005 | Shah et al. |
| 2005/0230365 A1 | 10/2005 | Lei et al. |
| 2005/0232313 A1 | 10/2005 | Fermann et al. |
| 2005/0248758 A1 | 11/2005 | Carron et al. |
| 2006/0000988 A1 | 1/2006 | Stuart et al. |
| 2006/0006964 A1 | 1/2006 | Huang et al. |
| 2006/0019171 A1 | 1/2006 | Hosono et al. |
| 2006/0028655 A1 | 2/2006 | Cordingley et al. |
| 2006/0032841 A1 | 2/2006 | Tan et al. |
| 2006/0039419 A1 | 2/2006 | Deshi |
| 2006/0051025 A1 | 3/2006 | Mizuuchi et al. |
| 2006/0056468 A1 | 3/2006 | Dantus et al. |
| 2006/0058683 A1 | 3/2006 | Chance |
| 2006/0066848 A1 | 3/2006 | Frankel |
| 2006/0071803 A1 | 4/2006 | Hamburger et al. |
| 2006/0096426 A1 | 5/2006 | Park |
| 2006/0096962 A1 | 5/2006 | Park |
| 2006/0119743 A1 | 6/2006 | Lin |
| 2006/0120412 A1 | 6/2006 | Liu |
| 2006/0134004 A1 | 6/2006 | Gellermann et al. |
| 2006/0169677 A1 | 8/2006 | Deshi |
| 2006/0187974 A1 | 8/2006 | Dantus |
| 2006/0207975 A1 | 9/2006 | Ehrmann et al. |
| 2006/0207976 A1 | 9/2006 | Bovatsek et al. |
| 2006/0243712 A1 | 11/2006 | Haight et al. |
| 2006/0274403 A1 | 12/2006 | Kaplan et al. |
| 2006/0285071 A1 | 12/2006 | Erickson et al. |
| 2007/0034615 A1 | 2/2007 | Kleine |
| 2007/0093970 A1 | 4/2007 | Padmanabhan et al. |
| 2007/0103778 A1 | 5/2007 | Kaplan et al. |
| 2008/0170218 A1 | 7/2008 | Dantus et al. |
| 2008/0309931 A1 | 12/2008 | Silberberg et al. |
| 2009/0122819 A1 | 5/2009 | Dantus et al. |
| 2009/0188901 A1 | 7/2009 | Dantus |
| 2009/0207869 A1 | 8/2009 | Dantus et al. |
| 2009/0238222 A1 | 9/2009 | Dantus et al. |
| 2009/0256071 A1 | 10/2009 | Dantus et al. |
| 2009/0257464 A1 | 10/2009 | Dantus et al. |
| 2011/0005090 A1 | 1/2011 | Lee et al. |

FOREIGN PATENT DOCUMENTS

| | | |
|---|---|---|
| EP | 1625939 A2 | 2/2006 |
| EP | 1742311 A1 | 1/2007 |
| JP | 01113189 A | 5/1989 |
| JP | 11095051 A | 4/1999 |
| JP | 2000055781 A | 2/2000 |
| JP | 2001337301 A | 12/2001 |
| JP | 2002139716 A | 5/2002 |
| JP | 2003-155256 A | 5/2003 |
| WO | WO 99/57318 | 11/1999 |
| WO | WO 00/70647 | 11/2000 |
| WO | WO 01/54323 | 7/2001 |
| WO | WO-0231799 A1 | 4/2002 |
| WO | WO 02/061799 | 8/2002 |
| WO | WO-2004023413 A2 | 3/2004 |
| WO | WO 2005/088783 | 9/2005 |
| WO | WO-2005111677 A2 | 11/2005 |
| WO | WO-2006079083 A2 | 7/2006 |
| WO | WO-2006111682 A1 | 10/2006 |
| WO | WO-2006138442 A2 | 12/2006 |
| WO | WO-2007001308 A2 | 1/2007 |
| WO | WO-2007002231 A1 | 1/2007 |
| WO | WO-2007028119 A2 | 3/2007 |
| WO | WO-2007064703 | 6/2007 |
| WO | WO-2007145702 A2 | 12/2007 |
| WO | WO-2008063602 A2 | 5/2008 |
| WO | WO-2009086122 A2 | 7/2009 |

OTHER PUBLICATIONS

Krampert, Gerhard, Femtosecond Quantum Control and Adaptive Polarization Pulse Shaping, 2004, pp. 1-135.*

Gerbasi et al., Theory of "laser distillation" of enantiomers: Purification of a racemic mixture of randomly oriented dimethylallene in a collisional environment, Feb. 17, 2006, Journal of Chemical Physics, vol. 124, pp. 1-9.*

Bychkov et al., Laser Distillation of Enantiomers from an Isotropic Racemic Mixture, Apr. 10, 2001, High Resolution Laser Spectroscopy, vol. 11, pp. 1088-1093.*

Salam et al., On the relative populations of excited state enantiomers, for randomly orientated molecules, obtained through the use of circularly polarized pulsed lasers, Oct. 3, 1997, Chem. Phys. Letters, vol. 277, pp. 199-207.*

Flores et al., Asymmetric Photolysis of RS-Leucine with Circularly Polarized Ultraviolet Light, Journal of American Chemical Society, May 25, 1977, pp. 3622-3625.*

(56) References Cited

OTHER PUBLICATIONS

Zeek, Erik; "Pulse Shaping for High-Harmonic Generation;" Dissertation Submitted in Partial Fulfillment of the Requirements for the Degree of Doctor of Philosophy (Applied Physics) in the University of Michigan, 2000; 126 pages.

Baltuška, Andrius et al.; "Visible Pulse Compression to 4 fs by Optical Parametric Amplification and Programmable Dispersion Control;" Optics Letters, vol. 27, No. 5, Mar. 1, 2002, pp. 306-308.

"Femtosource Scientific " brochure, Femtolasers Productions GmbH (believed to be published prior to Jan. 15, 2009) 2 pages.

Bonacina, Luigi, et al., "Multiobjective genetic approach for optimal control of photoinduced processes," Physical Review A. 76, The American Physical Society, (2007) pp. 023408-1 through 023408-5.

Bowlan, Pamela, et al., "Directly measuring the spatio-temporal electric field of focusing ultrashort pulses," Optics Express, vol. 15, No. 16 (2007) pp. 10219-10230.

Béjot, Pierre, et al., "Laser noise compression by filamentation at 400 nm in argon," Optics Express, vol. 15, No. 20 (Oct. 2007) pp. 13295-13309.

Chen, Bi-Chang, et al., "Characterization of a broadband pulse for phase controlled multiphoton microscopy by single beam Spider," Optics Letters, vol. 32, No. 16, Optical Society of America (Aug. 15, 2007) pp. 2411-2413.

Chung, Jung-Ho, "Ambiguity of Ultrashort Pulse Shapes Retrieved From the Intensity Autocorrelation and the Power Spectrum," IEEE Journal on Selected topics in Quantum Electronics, vol. 7, No. 4 (Jul./Aug. 2001) pp. 656-666.

Coello, Yves, "Interference without an interferometer: a different approach to measuring, compressing, and shaping ultrashort laser pulses," J. Opt. Soc. Am. B/vol. 25, No. 6 (Jun. 2008) pp. A140-A150.

Kubo, Atsushi, et al., "Femtosecond Imaging of Surface Plasmon Dynamics in a Nanostructured Silver Film," Nano Letters, vol. 5, No. 6 (2005) American Chemical Society, pp. 1123-1127.

Laarmann, T., et al., "Femtosecond pulse shaping as analytic tool in mass spectrometry of complex polyatomic systems," J Phys B-at Mol Opt 2008;41(7).

Lozovoy, Vadim V., et al., "Direct measurement of spectral phase for ultrashort laser pulses," Optics Express, vol. 16, No. 2 (Jan. 21, 2008) pp. 592-597.

May, Volkhard et al., "Theory of ultrafast nonresonant multiphoton transitions in polyatomic molecules: Basics and application to optimal control theory," J. Chem. Phys. 127 (2007) pp. 144102-1 through 144102-11.

Montgomery, Matthew A., "Elucidation of Control Mechanisms Discovered during Adaptive Manipulation of [Ru(dpb)3](PF6)2 emission in the Solution Phase," American Chemical Society, J. Phys. Chem. A, vol. 111, No. 8 (2007) pp. 1426-1433.

Nisoli, M., et al., "Generation of high energy 10 fs pulses by a new pulse compression technique," Appl. Phys. Lett., vol. 68, No. 20 (May 13, 1996) pp. 2793-2795.

Nuernberger, Patrick, "Femtosecond quantum control of molecular dynamics in the condensed phase," Invited Article, Physical Chemistry Chemical Physics, The Owner Societies, vol. 9 (2007) pp. 2470-297.

Oron, Dan, et al., "Scanningless depth-resolved microscopy," Optics Express, vol. 13, No. 5 (Mar. 7, 2005).

Tada, Junji, "Adaptively controlled supercontinuum pulse from a microstructure fiber for two-photon excited fluorescence microscopy," Applied Optics, vol. 46, No. 15, (May 20, 2007) pp. 3023-3030.

Urbasch, Gunter, et al., "Distinctino of ortho- and para-Xylene by Femtosecond-Laser Mass Spectrometry," Communications, ChemPhysChem vol. 8 (2007) Wiley-VCH Verlag GmbH&Co. KGaA, Weinheim, pp. 2185-2188.

Wang, He, et al., "Generation of 0.5 mJ, few-cycle laser pulses by an adaptive phase modulator," Optics Express, vol. 16, No. 19 (Sep. 15, 2008) pp. 14448-14455.

Wnuk, Pawel, et al., "Coherent control and dark pulses in second harmonic generation," Optics Communications 272, ScienceDirect (2007) pp. 496-502.

Zang, Hegui, et al., "Study on Frequency-doubling Effect of the Dually Doped KTP Crystals," Journal of Synthetic Crystals vol. 29, No. 2 (May 2000).

"Coherent® Silhouette, Ultrafast Pulse Shaper," Key Features brochure. Web. Jan. 29, 2008 http://vvww.coherent.com/Lasers/index.cfm?Fuseaction=show.print&ID=1485.

"Coherent® Silhouette, Ultrafast Pulse Shaping and Measurement," brochure, (2007) 2 pages. Coherent, Inc.

Takasago, Kazuya, et al., "Design of Frequency-Domain Filters for Femtosecond Pulse Shaping," Part 1, No. 2A (Feb. 1996)pp. 624-629. Jpn. J. Appl. Phys.

Zeek, E. et al., "Pulse Compression by Use of Deformable Mirrors," Optics Letters, OSA, Optical Society of America, vol. 24, No. 7, Apr. 1, 1999, pp. 493-495.

Sardesai, H et al. "A Femtosecond Code-Division Multiple-Access Communication System Test Bed," Journal of Lightwave Technology, IEEE Service Center, vol. 16, No. 11, Nov. 1, 1998, p. 1953-1964.

Comstock et al.; "Multiphoton intrapulse interference 6; binary phase shaping"; Optics Express Opt. Soc. America USA, vol. 12, No. 6, Mar. 22, 2004; pp. 1061-1066.

Hu et al.; "A New Nonlinear Optical Crystal-BaAlBO3F2(BABF)"; Japanese Journal of Applied Physics, vol. 41, No. 10B, Part 2, Oct. 15, 2002; pp. L1131-L1133.

Weiner et al.; "Shaping of femtosecond pulses using phase-only filters designed by simulated annealing"; Journal of the Optical Society of America A (Optics and Image Science) USA, vol. 10, No. 5, May 1993; pp. 1112-1120.

M. Dantus et al., "Experimental Coherent Laser Control of Physicochemical Processes", Chem. Rev. 2004, 104, pp. 1813-1859.

Dela Cruz, J. et al., "Use of coherent control methods through scattering biological tissue to achieve functional imaging," PNAs, vol. 101, No. 49, Dec. 7, 2004, pp. 16996-17001.

Weiner, A.M. et al. "Generation of terahertz-rate trains of femtosecond pulses by phase-only filtering," Optics Letters, vol. 15, No. 1, Jan. 1, 1990, pp. 51-53.

M. Hacker et al., "Iterative Fourier Transform Algorithm for Phase-Only Pulse Shaping", Optics Express, vol. 9, No. 4, Aug. 13, 2001, pp. 191-199.

R. Bartels et al., "Shaped-Pulse Optimization of Coherent Emission of High-Harmonic Soft X-Rays", 2000 Macmillan Magazines Ltd., Nature, vol. 406. Jul. 13, 2000, pp. 164-166.

H. Zou, C. Zhou, Femtosecond Pulse Shaping with Space-to-Time Conversion Based on Planar Optics, Optik Optics, ScienceDirect, 2006/2007, pp. 5-8.

S. Zhang, X. Zhang, J. Huang, L. Deng, Z. Sun, W. Zhang, Z. Wang, Z. Xu, R.Li, Coherent Enhancement of Broadband Frequency Up-Conversion in BBO Crystal by Shaping Femtosecond Laser Pulses, Optics Communications, ScienceDirect, 2006/2007, pp. 559-563.

Y. Oishi, A. Suda, F. Kannari, K. Midorikawa, Intense Femtosecond Pulse Shaping Using a Fused-Silica Spatial Light Modulator, Optics Communications, ScienceDirect, 2006/2007, pp. 305-309.

B. Xu, Y. Coello, V.Lozovoy, D. Harris; M. Dantus, Pulse Shaping of Octave Spanning Femtosecond Laser Pulses, Optics Express, vol. 14, No. 22, Oct. 30, 2006, six pages.

F.M. Reinert, M. Ninck, W. Lüthy, T. Feurer, Shaping a Femtosecond Pulse with a Programmable Thermo-Optically Driven Phase Modulator, Optics Express, vol. 15, No. 7, Apr. 2, 2007, six pages.

H. Miao, A. Weiner, C. Langrock, R. Roussev, M. Fejer, Sensing and Compensation of Femtosecond Waveform Distortion Induced by All-Order Polarization Mode Dispersion at Selected Polarization States, Optics Letters, vol. 32, No. 4, Feb. 15, 2007, pp. 424-426.

S. Nath, D. Urbanek, S. Kern, M. Berg, High-Resolution Raman Spectra with Femtosecond Pulses: An Example of Combined Time- and Frequency-Domain Spectroscopy, Physical Review Letters, 2006, pp. 267401-1 to 267401-4.

Feurer, T., et al.; "Coherent Control Over Collective Polariton Excitations: The Dawn of Polaritonics;" 2002 Thirteenth International Conference on Ultrafast Phenomena, Technical Digest (Tops vol. 72); Opt. Soc. America; XP008086358; pp. 541-545.

Sato, Masamichi, et al.; "Adaptive Pulse Shaping of Femtosecond Laser Pulses in Amplitude and Phase Through a Single-Mode Fiber

(56) References Cited

OTHER PUBLICATIONS by Referring to Frequency-Resolved Optical Gating Patterns;" Jpn. J. Appl. Phys., vol. 41 (2002); Part 1 No. 6A, Jun. 2002; XP-002436366; pp. 3704-3709.

Gee, S., et al.; "Ultrashort Pulse Generation by Intracavity Spectral Shaping and Phase Compensation of External-Cavity Modelocked Semiconductor Lasers;" IEEE Journal of Quantum Electronics, vol. 36, No. 9, Sep. 2000; XP-002462407; pp. 1035-1040.

Scaffidi, J., et al.; "Spatial and Temporal Dependence of Interspark Interactions in Femtosecond-Nanosecond Dual-Pulse Laser-Induced Breakdown Spectroscopy;" Applied Optics, vol. 43, No. 27, Sep. 20, 2004; XP-002462408; pp. 5243-5250.

Pfeiffer, W., et al.; "Ultrafast Spatio-Temporal Near-Field Control;" IEEE 2005 European Quantum Electronics Conference, 0-7803-8973-5/05; p. 169 (1 page).

Alexeev, I. et al.; "Ultraviolet Light Generation by Intense Laser Filaments Propagating in Air;" Conference on Lasers & Electro-Optics (CLEO), Baltimore, Maryland, USA, XP010876479; May 22-27, 2005; pp. 189-191.

Akozbek, N. et al.; "Continuum Generation of the Third-Harmonic Pulse Generated by an Intense Femtosecond IR Laser Pulse in Air;" Applied Physics B (Lasers and Optics), Springer-Verlag, Germany, vol. B77, No. 2-3, XP002476096; Sep. 2003; pp. 177-183.

Xu, B. et al.; "Pulse Shaping of Octave Spanning Femtosecond Laser Pulses;" Optics Express Opt. Soc. America USA, vol. 14, No. 22, XP002476097; Oct. 30, 2006; pp. 10939-10944.

Ting, A. et al.; "Remote Atmospheric Breakdown for Standoff Detection by Using an Intense Short Laser Pulse;" Applied Optics. Opt. Soc. America USA, vol. 44, No. 25, XP002476098; Sep. 1, 2005; pp. 5315-5320.

Lozovoy, V. V. et al.; "What Role Can Four-Wave Mixing Techniques Play in Coherent Control?;" Advances in Multiphoton Processes and Spectroscopy 14; and Quantum Control of Molecular Reaction Dynamics, edited by R. J. Gordon and Y. Fujimura, World Scientific, Singapore, 2000; pp. 62-79.

Dantus, Marcos; "Laser Control of Chemical Reactions;" Chemical & Engineering News, vol. 79, 2001; p. 191.

Pastirk, I. et al.; "Multidimensional Analytical Method Based on Binary Phase Shaping of Femtosecond Pulses;" J. Phys. Chem. A, vol. 109, No. 11, Feb. 23, 2005; pp. 2413-2416.

Pastirk, I. et al.; "Quantum Control of the Yield of a Chemical Reaction;" J. Chem. Phys., vol. 108, No. 11, Mar. 15, 1998; pp. 4375-4378.

Pastirk, I. et al.; "Sequences for Controlling Laser Excitation With Femtosecond Three-Pulse Four-Wave Mixing;" The Royal Society of Chemistry, vol. 113, 1999; pp. 401-424.

Pastirk, I. et al.; "Femtosecond Ground State Dynamics of Gas Phase $N^2O^4$ and $NO^2$;" Chemical Physics Letters, vol. 349, Nov. 23, 2001; pp. 71-78.

Pastirk, I. et al.: "Control and Characterization of Intramolecular Dynamics With Chirped Femtosecond Three-Pulse Four-Wave Mixing;" J. Phys. Chem. A, vol. 103, No. 49, Sep. 23, 1999; pp. 10226-10236.

Pastirk, I. et al.; "Femtosecond Photon Echo and Virtual Echo Measurements of the Vibronic and Vibrational Coherence Relaxation Times of Iodine Vapor;" Chemical Physics Letters, vol. 333, Jan. 5, 2001; pp. 76-82.

Dantus, Marcos; "Ahmed Zewail, Nobel Laureate in Chemistry;" European Photochemistry Association (EPA) Newsletter, No. 69, Jul. 2000; 5 pages.

Brown, E. J. et al.; "Femtosecond Transient-Grating Techniques: Population and Coherence Dynamics Involving Ground and Excited States;" J. Chem. Phys., vol. 110, No. 12, Mar. 22, 1999; pp. 5772-5788.

Brown, E. J. et al.; "Population and Coherence Control by Three-Pulse Four-Wave Mixing;" J. Chem. Phys., vol. 111, No. 9, Sep. 1, 1999; pp. 3779-3782.

Brown, E. J. et. al. "Ultrafast Rotational Anisotropy Measurements: Strong-Field Nonlinear Saturation Effects;" J. Phys. Chem. A, vol. 105, No. 34, 2001; pp. 8004-8010.

Brown, E. J. et. al. "Ultrafast Rotational Anisotropy Measurements: Unidirectional Detection;" J. Phys. Chem. A, vol. 103, No. 16, 1999; pp. 2912-2916.

Comstock, M. et al.; "Ultrafast Transient-Grating Study of Molecules After High Intensity Excitation;" in Ultrafast Phenomena XII, 2000; 2 pages.

Comstock, M. et al.; "Ultrafast Laser Induced Molecular Alignment and Deformation: Experimental Evidence From Neutral Molecules and From Fragment Ions;" J. Phys. Chem. A, vol. 107, No. 40, 2003; pp. 8271-8281.

Comstock, M. et al.; "Femtosecond Photon Echo Measurements of Electronic Coherence Relaxation Between The $X(^1Eg+)$ and $B(^3II_{0u}+)$ states of $I_2$ in the Presence of He, Ar, $N_2$, $O_2$, $C_3H_8$;" J. Chem. Phys., vol. 119, No. 13, Oct. 1, 2003; pp. 6546-6553.

Comstock, M. et al.; "Rotational Wavepacket Revivals for Phase Modulation of Ultrafast Pulses;" Chemical Physics Letters, 372, 2003; pp. 739-744.

Dela Cruz, J. M. et al.; "Quantitative Mass Spectrometric Identification of Isomers Applying Coherent Laser Control;" J. Phys. Chem. A, vol. 109, No. 38, Sep. 2005.

Rosker, M. J. et al.; "Femtosecond Clocking of the Chemical Bond;" Science, vol. 241, Sep. 2, 1988; pp. 1200-1202.

Rosker, M. J. et al.; "Femtosecond Real-Time Probing of Reactions. I. The Technique;" J. Chem. Phys., vol. 89, No. 10, Nov. 15, 1988; pp. 6113-6127.

Zhang, Q. et al.; "Femtosecond Dynamics of Photoinduced Molecular Detachment From Halogenated Alkanes. II. Asynchronous Concerted Elimination of $I_2$ From $CH_2I_2$;" J. Chem. Phys., vol. 109, No. 11, Sep. 15, 1998; pp. 4428-4442.

Zhang, Q. et al.; "Concerted Elimination Dynamics From Highly Excited States;" Faraday Discussions, 108, 1997; pp. 63-80.

Waner, M. J. et al.; "Imaging the Molecular Dimensions and Oligomerization of Proteins At Liquid/Solid Interfaces;" J. Phys. Chem. B, vol. 102, No. 9, 1998; pp. 1649-1657.

Choi, K-S et al.; "Charge Density Wave Caused by Reducing $ThSe_3$ by One Electron. Superstructure and Short-Range Order in $ATh_2Se_6$ (A = K, Rb) Studied by X-Ray Diffraction, Electron Diffraction, and Diffuse Scattering;" J. Am. Chem. Soc., vol. 120, No. 41, 1998; pp. 10706-10714.

Grimberg, B. I. et al.; "Ultrafast Nonlinear Spectroscopic Techniques in the Gas Phase and Their Density Matrix Representation;" J. Phys. Chem. A, vol. 106, No. 5, Feb. 7, 2002; pp. 697-718.

Gross, P. et al.; "Femtosecond Photoassociation: Coherence and Implications for Control in Bimolecular Reactions;" J. Chem. Phys., vol. 106, No. 19, May 15, 1997; pp. 8013-8021.

Peng, L. W. et al.; "Stepwise Solvation of the Intramolecular-Charge-Transfer Molecule $p$-(Dimethylamino)benzonitrile;" J. Phys. Chem., 91, 1987, p. 6162.

Marvet, Una et al.; "Femtosecond Dynamics of Unimolecular and Unrestricted Bimolecular Reactions;" J. Phys. Chem. A, vol. 102, No. 23, 1998; pp. 4111-4117.

Marvet, Una et al.; "Femtosecond Dynamics of Photoinduced Molecular Detachment From Halogenated Alkanes. I. Transition State Dynamics and Product Channel Coherence;" J. Chem. Phys., vol. 109, No. 11, Sep. 15, 1998.

Marvet, Una et al.; "Femtosecond Concerted Elimination of Halogen Molecules From Halogenated Alkanes;" Phys. Chem. Chem. Phys., 2, 2000; pp. 885-891.

Marvet, Una et al.; "Femtosecond Observation of a Concerted Chemical Reaction;" Chemical Physics Letters, 256, Jun. 21, 1996; pp. 57-62.

Marvet, Una et al.; "Femtosecond Photoassociation Spectroscopy: Coherent Bond Formation;" Chemical Physics Letters, 245, Nov. 3, 1995; pp. 393-399.

Dantus, Marcos; "Femtosecond Laser Pulses: Principles and Experiments;" (Book Review) J. Am. Chem. Soc., vol. 121, No. 37, 1999; pp. 8677-8678.

Dantus, Marcos et al.; "Ultrafast Spectroscopy;" Encyclopedia of Applied Physics, vol. 22, 1998; pp. 431-456.

Dantus, Marcos et al.; "Femtosecond Laser Observations of Molecular Vibration and Rotation;" Nature, vol. 343, Feb. 22, 1990; pp. 737-739.

(56) References Cited

OTHER PUBLICATIONS

Dantus, Marcos et al.; "Femtosecond Real-Time Probing of Reactions. V. The reaction of IHgI;" J. Chem. Phys., vol. 91, No. 12, Dec. 15, 1989; pp. 7437-7450.

Dantus, Marcos et al.; "Femtosecond Real-Time Probing of Reactions. II. The Dissociation Reaction of ICN;" J. Chem. Phys., vol. 89, No. 10, Nov. 15, 1988; pp. 6128-6140.

Dantus, Marcos et al.; "Real-Time Femtosecond Probing of "Transition States" In Chemical Reactions;" J. Chem. Phys., vol. 87, No. 4, Aug. 15, 1987; pp. 2395-2397.

Dantus, Marcos; "Ultrafast Probing and Control of Molecular Dynamics: Beyond the Pump-Probe Method;" Femtochemistry Wiley-VCH, Weinheim, 169, 2000; 35 pages.

Lozovoy, V. V. et al.; "Photon Echo Pulse Sequences With Femtosecond Shaped Laser Pulses As a Vehicle for Molecule-Based Quantum Computation;" J. Chemical Physics Letters 351, Jan. 10, 2002; pp. 213-221.

Lozovoy, V. V. et al.; "Systematic Control of Nonlinear Optical Processes Using Optimally Shaped Femtosecond Pulses;" ChemPhysChem, Wiley-VCH Verlag GmbH & Co. KGaA, Weinheim, 6, 2005; pp. 1970-2000.

Lozovoy, V. V. et al.: "Multiphoton Intrapulse Interference. IV. Ultrashort Laser Pulse Spectral Phase Characterization and Compensation;" Optics Letters, vol. 29, No. 7, Apr. 1, 2004; pp. 775-777.

Lozovoy, V. V. et al.; "Cascaded Free-Induction Decay Four-Wave Mixing;" Chemical Physics 266, 2001, pp. 205-212.

Lozovoy, V. V. et al.; "The Role of Pulse Sequences in Controlling Ultrafast Intramolecular Dynamics With Four-Wave Mixing;" Int. Rev. In Physical Chemistry, vol. 19, No. 4, 2000; pp. 531-552.

Lozovoy, V. V. et al.; "The Role of Microscopic and Macroscopic Coherence in Laser Control;" Chemical Physics 267, 2001; pp. 99-114.

Lozovoy, V. V. et al.; "Femtosecond Spectrally Dispersed Three-Pulse Four-Wave Mixing: The Role of Sequence and Chirp in Controlling Intramolecular Dynamics;" J. Raman Spectroscopy 31, 2000; pp. 41-49.

Pastirk, I. et al.; "2D (time-frequency) Femtosecond Four-Wave Mixing at $10^{14}$ W/cm$^2$: Molecular and Electronic Response;" Symposium on Optical Pulse and Beam Propagation III, Photonics West, 2001; 3 pages.

Lozovoy, V. V. et al.; "Laser Control of Physicochemical Processes; Experiments and Applications;" The Royal Society of Chemistry 2006, Annu. Rep. Prog. Chem., Sect. C, 102, www.rsc.org/annrepc, 2006; pp. 227-258.

Wefers, Marc M. et al.; "Generation of High-Fidelity Programmable Ultrafast Optical Waveforms;" Optics Letters, vol. 20, No. 9, May 1, 1995; pp. 1047-1049.

Brixner T. et al.; "Femtosecond Polarization Pulse Shaping;" Optics Letters, vol. 26, No. 8, Apr. 15, 2001; pp. 557-559.

Brixner T. et al.; "Adaptive Shaping of Femtosecond Polarization Profiles;" J. Opt. Soc. Am. B, vol. 20, No. 5, May 2003; pp. 878-881.

Suzuki, Takayuki et al.; "Nontrivial Polarization Shaping of Femtosecond Pulses by Reference to the Results of Dual-Channel Spectral Interferomtry;" Applied Optics, vol. 43, No. 32, Nov. 10, 2004; pp. 6047-6050.

Lim, Sang-Hyun et al.; "Single-Pulse Phase-Control Interferometric Coherent Anti-Stokes Raman Scattering Spectroscopy;" Physical Review A, 72, 2005; pp. 041803-1-041803-4.

Wollenhaupt, M. et al.; "Femtosecond Laser Photoelectron Spectroscopy on Atoms and Small Molecules: Prototype Studies in Quantum Control;" Annu. Rev. Phys. Chem., 56, 2005; pp. 25-56.

QWPO-AS, Zero Order Waveplates—Air Spaced, Optical Components and Assemblies, www.cvilaser.com, published Nov. 21, 2005; pp. 8-9.

PiStar Kinetic Circular Dichroism Spectrometer, http://www.phtophysics.com/pistar.php, Nov. 29, 2006; 3 pages.

Aviv Circular Dichroism Spectrometer, Model 400, Aviv Biomedical, Inc., http://www.avivbiomedical.com, Nov. 29, 2006; 2 pages.

Jasco Comparison Proven Spectroscopy & Chromatography Technology, J-815 Circular Dichroism Spectropolarimeter, Jasco UK, http://www.jasco.co.uk/j800.asp, Nov. 29, 2006, 2 pages.

Dong Gun Lee et al.; "Coherent Control of High-Order Harmonics with Chirped Femtosecond Laser Pulses"; Physical Review Letters, vol. 87, No. 24, Dec. 10, 2001; pp. 243902-1-243902-4.

M. Armstrong et al.; "Versatile seven-femtosecond pulse compressor of parametrically amplified pulses using adaptive optics: studies of the primary events in protein dynamics"; Applied Physics B 74 (Suppl), 2002; pp. S127-S132.

D.S. Chemla et al; "Ultrafast phase dynamics of coherent emission from excitons in GaAs quantum wells"; Physical Review B, vol. 50, No. 12, Sep. 15, 1995; pp. 8439-8453.

Jerome Tignon et al.; "Spectral Interferometry of Semiconductor Nanostructures"; IEEE Journal of Quantum Electronics, vol. 35, No. 4; Apr. 1999; pp. 510-522.

Arthur L. Smirl et al.; "Heavy-Hole and Light-Hole Quantum Beats in the Polarization State of Coherent Emission from Quantum Wells"; IEEE Journal of Quantum Electronics, vol. 35, No. 4; Apr. 1999; pp. 523-531.

John D. Hybl et al; "Two-dimensional Fourier transform electronic spectroscopy"; Journal of Chemical Physics, vol. 115, No. 14; Oct. 8, 2001; pp. 6606-6622.

C. Iaconis et al.; "Direct measurement of the two-point field correlation function"; Optics Letters, vol. 21, No. 21; Nov. 1, 1996; pp. 1783-1785.

A.M. Weiner et al.; "Femtosecond Pulse Sequences Used for Optical Manipulation of Molecular Motion"; Reports; Mar. 16, 1990; pp. 1317-1319.

Ch. Warmuth et al.; "Studying vibrational wavepacket dynamics by measuring fluorescence interference fluctuations"; Journal of Chemical Physics, vol. 112, No. 11; Mar. 15, 2000; pp. 5060-5069.

Ch. Warmuth et al.; "Molecular quantum dynamics in a thermal system: fractional wave packet revivals probed by random-phase fluorescence interferometry"; Journal of Chemical Physics, vol. 114, No. 22; Jun. 8, 2001; pp. 9901-9910.

G.G. Paulus et al.; "Absolute-phase phenomena in photoionization with few-cycle laser pulses"; Nature, vol. 414; Nov. 8, 2001; pp. 182-184.

M. Hentschel et al.; "Attosecond metrology"; Nature, vol. 414; Nov. 29, 2001; pp. 509-513.

L. Lepetit et al.; "Linear techniques of phase measurement by femtosecond spectral interferometry for applications in spectroscopy"; J. Opt. Soc. Am. B, vol. 12, No. 12; Dec. 1995; pp. 2467-2474.

L. Lepetit et al.; "Two-dimensional nonlinear optics using Fourier-transform spectral interferometry"; Optics Letters, vol. 21, No. 8; Apr. 15, 1996; pp. 564-566.

K.C. Chu et al.; "Temporal interferometric measurement of femtosecond spectral phase"; Optics Letters, vol. 21, No. 22; Nov. 15, 1996; pp. 1842-1844.

W.J. Walecki et al.; "Characterization of the polarization state of weak ultrashort coherent signals by dual-channel spectral interferometry"; Optics Letters, vol. 22, No. 2; Jan. 15, 1997; pp. 81-83.

J.P. Likforman et al.; "Measurement of photon echoes by use of femtosecond Fourier-transform Spectral Interferometry"; Optics Letters, vol. 22, No. 14; Jul. 15, 1997; pp. 1104-1106.

Michel F. Emde et al.; "Spectral interferometry as an alternative to time-domain heterodyning"; Optics Letters, vol. 22, No. 17; Sep. 1, 1997; pp. 1338-1340.

X. Chen et al.; "Temporally and spectrally resolved amplitude and phase of coherent four-wave-mixing emission from GaAs quantum wells"; Physical Review B, vol. 56, No. 15; Oct. 15, 1997; pp. 9738-9743.

Christophe Dorrer; "Influence of the calibration of the detector on spectral interferometry"; J. Opt. Soc. Am. B; vol. 16, No. 7; Jul. 1999; pp. 1160-1168.

Allison W. Albrecht et al.; "Experimental distinction between phase shifts and time delays: Implications for femtosecond spectroscopy and coherent control of chemical reactions"; Journal of Chemical Physics, vol. 111, No. 24; Dec. 22, 1999; pp. 10934-10955.

(56) References Cited

OTHER PUBLICATIONS

Christophe Dorrer et al.; "Spectral resolution and sampling issues in Fourier-transform spectral interferometry"; J. Opt. Soc. Am. B, vol. 17, No. 10; Oct. 2000; pp. 1795-1802.
G. Roberts; "Abstract-Interference effects in femtosecond spectroscopy"; Philosophical Transactions of the Royal Society of London Series A-Mathematical Physical and Engineering Sciences; 360 (1794): 987-1021; May 15, 2002 (1 page).
B. Chatel et al.; "Role of quadratic and cubic spectral phases in ladder climbing with ultrashort pulses"; Physical Review A 70; 2004; pp. 053414-1-053414-10.
Richard S. Judson et al.; "Teaching Lasers to Control Molecules"; Physical Review Letters, vol. 68, No. 10; Mar. 9, 1992; pp. 1500-1503.
Michael Messina et al.; "Quantum control of multidimensional systems: Implementation within the time-dependent Hartree approximation"; J. Chem Phys. 104; Jan. 1996; pp. 173-182.
D.H. Schirrmeister et al; "Femtosecond pulse dependence of dissipation in molecular systems"; Chemical Physics Letters Dec. 4, 1998; pp. 383-390.
Herschel Rabitz et al.; "Optimal Control of Molecular Motion: Design, Implementation and Inversion"; Acc. Chem. Res., vol. 33, No. 8; 2000; pp. 572-578.
R. deVivie-Riedle et al.; "Design and interpretation of laser pulses for the control of quantum systems"; Applied Physics B; 2000; pp. 285-292.
Moshe Shapiro et al.; On the Origin of Pulse Shaping Control of Molecular Dynamics; J. Phys. Chem. A, vol. 105, No. 105; 2001; pp. 2897-2902.
Y.J. Yan et al.; "Pulse shaping and coherent Raman spectroscopy in condensed phases"; J. Chem. Phys 94 (2); Jan. 15, 1991; pp. 997-1001.
Bern Kohler et al.; "Mode-Locking Matter with Light"; J. Phys. Chem 1993, 97; pp. 12602-12608.
Jeffrey L. Krause et al.; "Optical control of molecular dynamics: Molecular cannons, reflectrons and wave-packet focusers"; J. Chem. Phys. 99(9); Nov. 1, 1993; pp. 6562-6578.
V. Engel et al; "Two-photon wave-packet interferometry"; J. Chem Phys. 100 (8); Apr. 15, 1994; pp. 5448-5458.
Jeffrey L. Krause et al.; "Quantum Control of Molecular Dynamics: The Strong Response Regime"; J. Phys. Chem; 1995, 99; pp. 13736-13747.
Jianwei Che et al.; "Detection and Control of Molecular Quantum Dynamics"; J. Phys. Chem.; 1995; pp. 14949-14958.
M. Sterling et al.; "Interrogation and control of condensed phase chemical dynamics with linearly chirped pulses: 12 in solid Kr"; J. Chem. Phys. 104; May 1, 1996; pp. 6497-6506.
Jianwei Che et al.; "Semiclassical Dynamics and Quantum Control in Condensed Phases: Application to 12 in a Solid Argon Matrix"; J. Phys. Chem. 1996, 100; pp. 7873-7883.
Jianshu Cao et al.; "A simple physical picture for quantum control of wave packet localization"; J. Chem Phys., 107; Aug. 1, 1997; pp. 1441-1450.
Kenji Mishima et al.; "A theoretical study on laser control of a molecular nonadiabatic process by ultrashort chirped laser pulses"; Journal of Chemical Physics, vol. 109., No. 5; Aug. 1, 1998; pp. 1801-1809.
H.A. Kim et al.; "Expanded concept of the adiabatic population transfer using dressed states"; Physical Review A, vol. 59, No. 2; Feb. 1999; pp. 1404-1407.
Jianshu Cao et al.; "Molecular pie pulses: Population inversion with positively chirped short pulses"; Journal of Chemical Physics, vol. 113, No. 5; Aug. 1, 2000; pp. 1898-1909.
A.J. Wurzer et al.; "Highly localized vibronic wavepackets in large reactive molecules"; Applied Phys. B 71, 2000; pp. 405-409.
F. Legare et al.; "Laser pulse control of Raman processes by chirped non-adiabatic passage"; Journal of Raman Spectroscopy; 2000; pp. 15-23.

Moshe Shapiro et al.; "Coherently Controlled Asymmetric Synthesis with Achiral Light"; Physical Review Letters, vol. 84, No. 8; Feb. 21, 2000; pp. 1669-1672.
Gabriel Turinici et al.; "Quantum wavefunction controllability"; Chemical Physics 267; 2001; pp. 1-9.
M. Gruebele; "Fully quantum coherent control"; Chemical Physics 267; 2001; pp. 33-46.
V.S. Malinovsky et al.; "General theory of population transfer by adiabatic rapid passage with intense, chirped laser pulses"; The European Physical Journal D 14; 2001; pp. 147-155.
Z.W. Shen et al.; "Selective preparation of ground state wave-packets: a theoretical analysis of femtosecond pump-dump-probe experiments on the potassium dimmer"; The European Physical Journal D 14; 2001; pp. 167-172.
Sanislav S. Bychkov et al.; "Laser coherent control of molecular chiral states via entanglement of the rotational and torsional degrees of freedom"; Journal of Raman Spectroscopy; 2002; pp. 962-973.
S.E. Harris; "Control of Feshbach resonances by quantum interference"; Physical Review A66; 2002; pp. 010701-1-010701-4.
John M. Jean et al.; "Application of a multilevel Redfield theory to electron transfer in condensed phases"; J. Chem. Phys. 96; Apr. 15, 1992; pp. 5827-5842.
Bjarne Amstrup et al.; "Control of HOD photodissociation dynamics via bond-selective infrared multiphoton excitation and a femtosecond ultraviolet laser pulse"; J. Chem. Phys., vol. 97, No. 11; Dec. 1, 1992; pp. 8285-8295.
L D. Ziegler et al.; "Nonlinear polarization description of phase-locked pulse-pair spectroscopy"; J. Chem. Phys., vol. 97, No. 7; Oct. 1, 1992; pp. 4704-4713.
S. Meyer et al.; "Photoelectron distributions from femtosecond pump/probe excitation with chirped probe pulses"; Journal of Chemical Physics, vol. 108, No. 18; pp. 7631-7636.
V.M. Akulin et al.; "Laser Control of Atomic Motion inside Diatomic Molecules"; J. Phys. Chem. A, vol. 102, No. 23; 1998; pp. 4310-4320.
Jianshu Cao et al.; "Molecular Pi Pulse for Total Inversion of Electronic State Population"; Physical Review Letters, vol. 80, No. 7; Feb. 16, 1998; pp. 1406-1409.
Moshe Shapiro et al.; "Nonadiabatic wave packet dynamics: Experiment and theory in IBr"; Journal of Chemical Physics, vol. 110, No. 5; Feb. 1, 1999; pp. 2465-2473.
Zhenwen Shen et al.; "Pump-dump control and the related transient absorption spectroscopies"; Journal of Chemical Physics, vol. 110, No. 15; Apr. 15, 1999; pp. 7192-7201.
Kenji Mishima et al.; "Theoretical study on quantum control of photodissociation and photodesorption dynamics by femtosecond chirped laser pulses"; Journal of Chemical Physics, vol. 110, No. 16; Apr. 22, 1999; pp. 7756-7769.
H.S. Moon et al.; "Coherence control using the ratio of Rabi frequencies for complete coherent inversion in a four-level system"; J. Phys. B At. Mol. Phys. vol. 32; 1999; pp. 987-999.
Jeffrey A. Cina; "Nonlinear wavepacket interferometry for polyatomic molecules"; Journal of Chemical Physics, vol. 113, No. 21; Dec. 1, 2000; pp. 9488-9496.
F. Gelmukhanov et al.; "Dynamics of two-photon absorption by molecules and solutions"; J. Opt. Soc. Am. B, vol. 19, No. 5, May 2002; pp. 937-945.
Philip H. Bucksbaum; "Ultrafast control"; Nature magazine, vol. 421; Feb. 6, 2003; pp. 593-594. Kuhn & Weyn SR2 Sep. 4, 2001.
Christopher J. Bardeen et al.; "Effec of Pulse Shape on the Efficiency of Multiphoton Processes: Implications for Biological Microscopy"; Journal of Biomedical Optics, vol. 4, No. 3; Jul. 1999; pp. 362-367.
T. Hornung et al.; "Optimal control of one- and two-photon transitions with shaped femtosecond pulses and feedback"; Applied Physics B 71; 2000; pp. 277-284.
T. Brixner et al.; "Photoselective adaptive femtosecond quantum control in the liquid phase"; Nature magazine, vol. 414; Nov. 2001; pp. 57-60.
B.J. Pearson et al.; "Coherent control using adaptive learning algorithms"; Physical Review A, vol. 63; 2001; pp. 063412-1-063412-12.
Jennifer L. Herek et al.; "Quantum control of energy flow in light harvesting"; Nature magazine, vol. 417; May 30, 2002; pp. 533-535.

(56) References Cited

OTHER PUBLICATIONS

Nirit Dudovich et al.; "Single-pulse coherently controlled nonlinear Raman spectroscopy and microscopy"; Nature magazine, vol. 418; Aug. 1, 2002; pp. 512-514.
Dan Oron et al.; "Single-Pulse Phase-Contrast Nonlinear Raman Spectroscopy"; Physical Review Letters, vol. 89, No. 27; Dec. 30, 2002; pp. 27300-1-273001-4.
T. Brixner et al.; "Liquid-phase adaptive femtosecond quantum control: Removing intrinsic intensity dependencies"; Journal of Chemical Physics, vol. 118, No. 8; Feb. 22, 2003; pp. 3692-3701.
R. Netz et al.; "Observation of Selectivity of Coherent Population Transfer Induced by Optical Interference"; Physical Review Letters, vol. 90, No. 6; Feb. 14, 2003; pp. 063001-1-063001-4.
D.W. Schumacher et al.; "Phase Dependence of Intense Field Ionization"; Physical Review A, vol. 54, No. 5; Nov. 1996; pp. 4271-4278.
Christopher J. Bardeen et al.; "Feedback quantum control of molecular electronic population transfer"; Chemical Physics Letters 280; 1997; pp. 151-158.
Christopher J. Bardeen et al.; "Quantum Control of Population Transfer in Green Fluorescent Protein by Using Chirped Femtosecond Pulses"; J. Am. Chem. Soc., vol. 120, No. 50; 1998; 13023-13027.
Doron Meshulach et al.; "Coherent quantum control of two-photon transitions by a femtosecond laser pulse"; Nature magazine, vol. 396; Nov. 19, 1998; pp. 239-242.
A. Baltuska et al.; "Attosecond control of electronic processes by intense light fields"; Nature magazine, vol. 421; Feb. 6, 2003; pp. 611-615.
D.J. Maas et al.; "Population transfer via adiabatic passage in the rubidium quantum ladder system"; Physical Review A, vol. 59, No. 2; Feb. 1999; pp. 1374-1381.
Zohar Amitay et al.; "Phase-tailoring molecular wave packets to time shift their dynamics"; Chemical Physics 267; 2001; pp. 141-149.
T.C. Weinacht et al.; "Coherent learning control of vibrational motion in room temperature molecular gases"; Chemical Physics Letters 344; 2001; pp. 333-338.
R. van Leeuwen et al.; "Manipulation of differential electron yields via autoionizing wave-packet control"; Physical Review A, Vol, 63; 2001; pp. 033403-1-033403-5.
Dan Oron et al.; "Quantum control of coherent anti-Stokes Raman processes"; Physical Review A, vol. 65; 2002; pp. 043408-1-043408-4.
Nirit Dudovich et al.; "Coherent Transient Enhancement of Optically Induced Resonant Transitions"; Physical Review Letters, vol. 88, No. 12; Mar. 25, 2002; pp. 123004-1-123004-4.
Jerome Degert et al.; "Realization of a Time-Domain Fresnel Lens with Coherent Control"; Physical Review Letters, vol. 89, No. 20; Nov. 11, 2002; pp. 203003-1-203003-4.
M. Wollenhaupt et al.; "Interferences of Ultrashort Free Electron Wave Packets"; Physical Review Letters, vol. 89, No. 17; Oct. 21, 2002; pp. 173001-1-173001-4.
R. Teets et al.; "Coherent Two-Photon Excitation by Multiple Light Pulses"; Physical Review Letters, vol. 38, No. 14; Apr. 4, 1977; lags. 760-764.
R.R. Jones; "Multiphoton Ionization Enhancement Using Two Phase-Coherent Laser Pulses"; Physical Review Letters, vol. 75, No. 8; Aug. 21, 1995; pp. 1491-1494.
D.J. Maas et al.; "Vibrational ladder climbing in NO By ultrashort infrared laser pulses"; Chemical Physics Letters 270; May 16, 1997; pp. 45-49.
Christopher J. Bardeen et al.; "Quantum control of I2 in the gas phase and in condensed phase solid Kr matrix"; J. Chem. Phys., vol. 106, No. 20; May 22, 1997; pp. 8486-8503.
D.J. Maas et al.; Vibrational ladder climbing in NO By (sub)picosecond frequency-chirped infrared laser pulses'; Chemical Physics Letters 290; 1998; pp. 75-80.
Vladislav V. Yakovlev et al.; "Chirped pulse enhancement of multiphoton absorption in molecular iodine"; Journal of Chemical Physics, vol. 108, No. 6, Feb. 8, 1998; pp. 2309-2313.
Radoslaw Uberna et al.; "Phase and amplitude control in the formation and detection of rotational wave packets in the E1Eg state of Li2"; Journal of Chemical Physics, vol. 108, No. 22; pp. 9259-9274.
John M. Papanikolas et al.; "Erratum: Manipulation of rovibrational wave packet composition in the Li2 E(Eg) shelf state using intermediate state selection and shaped femtosecond laser pulses"; J. Chem Phys. 107, 4172; 1997; p. 10830.
T.C. Weinacht et al.; "Measurement of the Amplitude and Phase of a Sculpted Rydberg Wave Packet"; Physical Review Letters; vol. 80, No. 25; Jun. 22, 1998; pp. 5508-5511.
Radoslaw Uberna et al.; "Phase control of wavepacket dynamic using shape femtosecond pulses"; Faraday Discuss, vol. 113; 1999; pp. 385-400.
T.C. Weinacht et al.; "Toward Strong Field Mode-Selective Chemistry"; J. Phys. Chem. A, vol. 103, No. 49; 1999; pp. 10166-10168.
Mohamed Aziz Bouchene et al.; "Wavepacket interferometry with chirped pulses"; J. Phys. B At. Mol. Opt. Phys. 32; 1999; pp. 5167-5177.
D.J. Maas et al.; "Rotational interference in vibrational ladder climbing in NO by chirped infrared laser pulses"; Physical Review A, vol. 60, No. 2; Aug. 1999; pp. 1351-1362.
R. van Leeuwen et al.; "Coherent Control of the Energy and Angular Distribution of Autoionized Electrons"; Physical Review Letters, vol. 82, No. 14; Apr. 5, 1999; pp. 2852-2855.
Celine Nicole et al.; "Saturation of wave-packet interferences: Direct observation of spin precession in potassium atoms"; Physical Review A, vol. 60, No. 3; Sep. 1999; pp. R1755-R1758.
Mohamed Aziz Bouchene et al.; "Interplay between wave packet interferences and second harmonic generation"; Optics Communications 181; 2000; pp. 327-336.
Radoslaw Uberna et al.; "Ultrafast spectroscopy of wavelength-dependent coherent photoionization cross sections of Li2 wave packets in the E1Eg state: The role of Rydberg states"; Journal of Chemical Physics, vol. 114, No. 23; Jun. 15, 2001; pp. 10311-10320.
Lorenzo Pesce et al.; "Quantum dynamics simulation of the ultrafast photoionization of Li2"; Journal of Chemical Physics, vol. 114, No. 3; Jan. 15, 2001; pp. 1259-1271.
M.F. DeCamp et al.; "Dynamics and coherent control of high-amplitude optical phonons in bismuth"; Physical Review B, vol. 64; 2001; pp. 092301-1-092301-3.
J. Ahn et al.; "Quantum Phase Retrieval of a Rydberg Wave Packet Using a Half-Cycle Pulse"; Physical Review Letters, vol. 86, No. 7; Feb. 12, 2001; pp. 1179-1182.
Sebastien Zamith et al.; "Observation of Coherent Transients in Ultrashort Chirped Excitation of an Undamped Two-Level System"; Physical Review Letters, vol. 87, No. 3; Jul. 16, 2001; pp. 033001-1-033001-4.
Hans U. Stauffer et al.; "Simultaneous phase control of Li2 wave packets in two electronic states"; Journal of Chemical Physics, vol. 116, No. 3; Jan. 15, 2002; pp. 946-954.
Joshua B. Ballard et al.; "Optimization of wave packet coefficients in Li 2 using an evolutionary algorithm: The role of resonant and nonresonant wavelengths"; Journal of Chemical Physics, vol. 116, No. 4; Jan. 22, 2002; pp. 1350-1360.
Elizabeth Mirowski et al.; "Effect of nonresonant frequencies on the enhancement of quantum beat amplitudes in rovibrational states of Li2: The role of state spacing"; Journal of Chemical Physics, vol. 117, No. 24; Dec. 22, 2002; pp. 11228-11238.
S.N. Pisharody et al.; "Phase-controlled stair-step decay of autoionizing radial wave packets"; Physical Review A, vol. 65; 2002; pp. 033418-1-033418-10.
R. Netz et al.; "Coherent population dynamics of a three-level atom in spacetime"; Physical Review A, vol. 65; pp. 043406-1-043406-12.
Joshua B. Ballard et al.; "Simultaneous control of time-dependent population transfer dynamics and wave-packet quantum interferences in Li2 by shaped ultrafast pulses"; Physical Review A 66; 2002; pp. 043402-1-043402-7.
Dan Oron et al.; "Narrow-Band Coherent Anti-Stokes Raman Signals from Broad-Band Pulses"; Physical Review Letters, vol. 88, No. 6; Feb. 11, 2002; pp. 063004-1-063004-4.
M.M. Salour et al.; "Observation of Ramsey's Interference Fringes in the Profile of Doppler-Free Two-Photon Resonances"; Physical Review Letters, vol. 38, No. 14; Apr. 4, 1977; pgs. 757-760.

(56) References Cited

OTHER PUBLICATIONS

N.F. Scherer et al.; "Time resolved dynamics of isolated molecular systems studied with phase-locked femtosecond pulse pairs"; J. Chem Phys. vol. 93, No. 1; Jul. 1, 1990; pp. 856-857.
J.S. Melinger et al.; "Adiabatic population inversion in I2 vapor with picosecond laser pulses"; J. Chem Phys. vol. 95, No. 3; Aug. 1, 1991; pp. 2210-2213.
J.J. Gerdy et al.; "Femtosecond selective control of wave packet population"; Chemical Physics Letters, vol. 171, No. 1/2; Jul. 27, 1990; pp. 1-4.
Norbert F. Scherer et al.; "Fluorescence-detected wave packet interferometry: Time resolved molecular spectroscopy with sequences of femtosecond phase-locked pulses"; J. Chem. Phys., vol. 95, No. 3; Aug. 1, 1991; pp. 1487-1511.
N.F. Scherer et al.; "Fluorescence-detected wave packet interferometry. II. Role of rotations and determination of the susceptibility"; J. Chem. Phys., vol. 96, No. 6; Mar. 15, 1992; pp. 4180-4194.
L.D. Noordam et al.; "Redistribution of Rydberg States by Intense Picosecond Pulses"; Physical Review Letters, vol. 68, No. 10; Mar. 9, 1992; pp. 1496-1499.
J.S. Melinger et al.; "Generation of Narrowband Inversion with Broadband Laser Pulses"; vol. 68, No. 13; Mar. 30, 1992; pp. 2000-2003.
B. Broers et al.; "Efficient Population Transfer in a Three-Level Ladder System by Frequency-Swept Ultrashort Laser Pulses"; Physical Review Letters, vol. 69, No. 14; Oct. 5, 1992; pp. 2062-2065.
R.R. Jones et al.; "Ramsey Interference in Strongly Driven Rydberg Systems"; Physical Review Letters, vol. 71, No. 16; Oct. 18, 1993; pp. 2575-2578.
J.F. Christian et al.; "Rubidium electronic wavepackets probed by a phase-sensitive pump-probe technique"; Optics Communications, vol. 103, No. 1/2; Nov. 1, 1993; pp. 79- 84.
J.S. Melinger et al.; "Adiabatic population transfer with frequency-swept laser pulses"; J. Chem. Phys. vol. 101, No. 8; Oct. 15, 1994; pp. 6439-6454.
P. Balling et al.; "Interference in climbing a quantum ladder system with frequency-chirped laser pulses"; Physical Review A, vol. 50, No. 5; Nov. 1994; pp. 4276-4285.
D.W. Schumacher et al.; "Phase Dependence of Intense Field Ionization: A Study Using Two Colors"; Physical Review Letters, vol. 73, No. 10; Sep. 5, 1994; pp. 1344-1347.
L. Marmet et al.; "Observation of Quasi-Landau Wave Packets"; Physical Review Letters, vol. 72, No. 24; Jun. 13, 1994; pp. 3779-3782.
Valerie Blanchet et al.; "One-color coherent control in Cs2 Observation of 2.7 fs beats in the ionization signal"; Chemical Physics Letters, vol. 233; Feb. 25, 1995; pp. 491-499.
R.R. Jones et al.; "Bound-state interferometry using incoherent light"; J. Phys. B 28 At. Mol. Opt. Phys.; 1995; pp. L405-L411.
D.W. Schumacher et al.; "Programmable cesium Rydberg wave packets"; Physical Review A, vol. 52, No. 6; Dec. 1995; pp. 4719-4726.
R.R. Jones; "Interference Effects in the Multiphoton Ionization of Sodium"; Physical Review Letters, vol. 74, No. 7; Feb. 13, 1995; pp. 1091-1094.
Bern Kohler et al.; "Quantum Control of Wave Packet Evolution with Tailored Femtosecond Pulses"; Physical Review Letters, vol. 74, No. 17; Apr. 24, 1995; pp. 3360-3363.
M. Ovchinnikov et al.; "Quantum interference in resonant Raman spectra of I2 in condensed media"; J. Chem. Phys., vol. 106, No. 13; Apr. 1, 1997; pp. 5775-5778.
Richard M. Williams et al.; "Compositional control of rovibrational wave packets in the E(1 Eg) "shelf" state of Li2 via quantum-state-resolved intermediate state selection"; J. Chem. Phys. vol. 106, No. 20; May 22, 1997; pp. 8310-8323.
John M. Papanikolas et al.; "Manipulation of rovibrational wave packet composition in the Li2 E(1Eg) shelf state using intermediate state selection and shaped femtosecond laser pulses"; J. Chem. Phys., vol. 107, No. 11; Sep. 15, 1997; pp. 4172-4178.

Valerie Blanchet et al.; "Temporal Coherent Control in Two-Photon Transitions: From Optical Interferences to Quantum Interferences"; Physical Review Letters, vol. 78, No. 14; Apr. 7, 1997; pp. 2716-2719.
R. Zadoyan et al.; "Wavepacket diagnosis with chirped probe pulses"; Chemical Physics, vol. 233; 1998; pp. 353-363.
M.A. Bouchene et al.; "Temporal coherent control induced by wave packet interferences in one and two photon atomic transitions"; The European Physical Journal D, vol. 2; 1998; pp. 131-141.
Valerie Blanchet et al.; "Temporal coherent control in the photoionization of Cs2: Theory and experiment"; Journal of Chemical Physics, vol. 108, No. 12; Mar. 22, 1998; pp. 4862-4876.
R.A. Bartels et al.; "Nonresonant Control of Multimode Molecular Wave Packets at Room Temperature"; Physical Review Letters, vol. 88, No. 3; Jan. 21, 2002; pp. 033001-1 through 033001-4.
T. Brixner et al.; "Abstract- Femtosecond quantum control"; Advances in Atomic, Molecular, and Optical Physics, vol. 46; 46: 1-54; 2001 (1 page).
T. Brixner et al.; "Abstract-Photoselective adaptive femtosecond quantum control in the liquid phase"; Nature; 414 (6859): 57-60; Nov. 1, 2001 (1 page).
B. Dayan et al.; "Coherent control with broadband squeezed vacuum"; arXiv:quant-ph/0302038 v1; Feb. 5, 2003 (4 pages).
B. Dayan et al.; "Two Photon Absorption and Coherent Control with Broadband Down-Converted Light"; Physical Review Letters, vol. 93, No. 2; Jul. 9, 2004; pp. 023005-1-023005-4.
B. Dayan et al.; "Nonlinear Interactions with an Ultrahigh Flux of Broadband Entangled Photons"; Physical Review Letters, PRL 94; Feb. 4, 2005, 2004; pp. 043602-1043602-4.
N. Dudovich et al.; "Single-pulse coherent anti-Stokes Raman spectroscopy in the fingerprint spectral region"; J. of Chem. Phys., vol. 118, No. 20; May 22, 2003; pp. 9208-9215.
D. Oron et al.,; "Femtosecond Phase-and-Polaration Control for Background-Free Coherent Anti-Stokes Raman Spectroscopy"; Physical Review Letters, vol. 90, No. 21; May 30, 2003; pp. 213902-1-213902-4.
N. Dudovich et al.; "Quantum Control of the Angular Momentum Distribution in Multiphoton Absorption Processes"; Physical Review Letters, vol. 93, No. 10; Mar. 12, 2004; pp. 103003-1-103003-4.
D. Oron et al.,; "All-optical processing in coherent nonlinear spectroscopy"; Physical Review A 70; 2004; pp. 023415-1-023415-4.
J.G. Underwood et al.,; "Switched Wave Packets: A Route to Nonperturbative Quantum Control"; Physical Review Letters, vol. 90, No. 22; Jun. 6, 2003; pp. 223001-1-223001-4.
M. Renard et al.; "Controlling ground-state rotational dynamics of molecules by shaped femtosecond laser pulses"; Physical Review A 69; 2004; 043401-1-043401-6.
A. Powe et al.; "Molecular Fluorescence, Phosphorescence, and Chemiluminescence Spectrometry"; Anal. Chem., vol. 76, No. 15; Aug. 15, 2004; pp. 4614-4634.
D. Abramavicius et al.; "Disentangling multidimensional femtosecond spectra of excitons by pulse shaping with coherent control"; J. of Chem. Phys., vol. 120, No. 18; May 8, 2004; pp. 8373-8378.
M.C. Chen et al.; "Coherent control multiphoton processes in semiconductor saturable Bragg reflector with freezing phase algorithm"; Appl. Phys. B 80; 2005; pp. 333-340.
W. Wohlleben et al.; "Coherent Control for Spectroscopy and Manipulation of Biological Dynamics"; Chem. Phys. Chem., 6; 2005; pp. 850-857.
T. Okada et al.; "Optical control of two-photon excitation efficiency of α-perylene crystal by pulse shaping"; Amer. Inst. of Phys., vol. 121, No. 13; Oct. 1, 2004; pp. 6386-6391.
V. Prokhorenko et al.; "Coherent control of the population transfer in complex sovated molecules at weak excitation. An experimental study"; The J. of Chem. Phys., 122; 2005; 184502-1-184502-11.
A. Prakelt et al.; "Phase control of two-photon transition with shaped femtosecond laser-pulse sequences"; Physical Review A 70; 2004; pp. 063407-1-06407-10.
B.J. Pearson et al.; "Control of Raman Lasing in the Nonimpulsive Regime"; Physical Review Letters, vol. 92, No. 24; Jun. 18, 2004; pp. 243003-1-243003-4.

(56) References Cited

OTHER PUBLICATIONS

Derryck T. Reid; "Algorithm for Complete and Rapid Retrieval of Ultrashort Pulse Amplitude and Phase from a Sonogram"; IEEE Journal of Quantum Electronics; vol. 35, No. 11, Nov. 1999; pp. 1584-1589.

I.G. Cormack et al.; "Rapid measurement of ultrashort-pulse amplitude and phase from a two-photon absorption sonogram trace"; J. Opt. Soc. Am. B; vol. 18, No. 9, Sep. 2001; pp. 1377-1382.

E. Tokunaga et al.; "Frequency-domain interferometer for femtosecond time-resolved phase spectroscopy"; Optics Letters, vol. 17, No. 16; Aug. 15, 1992, pp. 1131-1133.

Victor Wong et al.; "Analysis of ultrashort pulse-shape measurement using linear interferometers"; Optics Letters, vol. 19, No. 4; Feb. 15, 1994; pp. 287-289.

Victor Wong et al.; "Linear filter analysis of methods for ultrashort-pulse-shape measurements"; J. Opt.Soc. Am. B, vol. 12, No. 8; Aug. 1995; pp. 1491-1499.

David M. Jonas et al.; "Femtosecond Wavepacket Spectroscopy: Influence of Temperature, Wavelength and Pulse Duration"; J. Phys. Chem.; 1995; pp. 2594-2608.

J. Peatross et al.; "Temporal decorrelation of short laser pulses"; J. Opt. Soc. Am. B, vol. 15, No. 1; Jan. 1998; pp. 216-222.

McGraw-Hill Encyclopedia of Science & Technology, 6th Ed.; "Mass spectrometry"; 1987; pp. 492-502 (12 pages).

Ocean Optics Inc.; "HR4000 High-resolution Spectrometer" http://oceanoptics.com/products/hr4000.asp; Jun. 25, 2005 (p. 1 of 4-p. 4 of 4).

Ocean Optics Inc.; "USB2000 Miniature Fiber Optic Spectrometer" http://oceanoptics.com/products/usb2000.asp; Jun. 25, 2005 (p. 1 of 7-p. 6 of 7).

Ocean Optics Inc., "S2000 Miniature Fiber Optic Spectrometer" http://oceanoptics.com/products/s2000.asp; Jun. 25, 2005 (p. 1 of 4-p. 4 of 4).

M. Schurenberg et al.; "Abstract-Laser desorption/ionization mass spectrometry of peptides and proteins with particle suspension matrixes"; Analytical Chemistry; 71 (1): 221-229; Jan. 1, 1999 (1 page).

F. Hillenkamp et al.; "Abstract-Matrix-assisted laser desorption/ionisation, an experience"; International Journal of Mass Spectrometry; 200 (1-3): 71-77; Dec. 25, 2000 (1 page).

M.O. Scully, et al.; "Fast Cars: Engineering a laser spectroscopic technique for rapid identification of bacterial spores"; PNAS; vol. 99, No. 17; Aug. 20, 2002; pp. 10994-11001.

K.D. Belfield et al.; "Multiphoton-absorbing organic materials for microfabrication, emerging optical applications and non-destructive three-dimensional imaging"; J. of Phys. Organic Chem., 13; 2000; pp. 837-849.

B. Natarajan et al.; "Abstract-Innovative pulse shaping for high-performance wireless TDMA"; IEEE Communications Letters; 5 (9): 372-374; Sep. 2001 (1 page).

A. Pe're et al.; Optical Code-Division Multiple Access Using Broad-Band Parametrically Generated Light; J. of Lightwave Tech.; vol. 22, No. 6; Jun. 2004; pp. 1463-1471.

J.J. Garcia-Ripoll et al.; "Speed Optimized Two-Qubit Gates with Laser Coherent Control Techniques for Ion Trap Quantum Computing"; Physical Review Letters, vol. 91, No. 15; Oct. 10, 2003; pp. 157901-1-157901-4.

J. Ahn et al.; "Information Storage and Retrieval Through Quantum Phase"; Science Magazine, vol. 287; Jan. 21, 2000; pp. 463-465.

Greg Taft et al.; "Measurement of 10-fs Laser Pulses"; IEEE Journal of Selected Topics in Quantum Electronics, vol. 2, No. 3, Sep. 1996; pp. 575-585.

Daniel J. Kane et al.; "Simultaneous measurement of two ultrashort laser pulses from a single spectrogram in a single shot"; Optical Society of America; vol. 14, No. 4, Apr. 1997; pp. 935-943.

Peter J. Delfyett et al.; "Joint Time-Frequency Meaurements of Mode-Locked Semiconductor Diode Lasers and Dynamics Using Frequency-Resolved Optical Gating"; IEEE Journal of Quantum Electronics, vol. 35, No. 4; Apr. 1999; pp. 487-500.

David N. Fittinghoff et al.; "Frequency-Resolved Optical Gating Measurement of Ultrashort Pulses Passing Through a High Numerical Aperture Objective"; IEEE Journal of Quantum Electronics, vol. 35, No. 4, Apr. 1999; pp. 479-486.

Andrius Baltuska et al.; "Second-Harmonic Generation Frequency-Resolved Optical Gating in the Single-Cycle Regime"; IEEE Journal of Quantum Electronics, vol. 35, No. 4, Apr. 1999; pp. 459-478.

Hilary K. Eaton et al.; "Investigating Nonlinear Femtosecond Pulse Propagation with Frequency-Resolved Optical Gating"; IEEE Journal of Quantum Electronics, vol. 35, No. 4, Apr. 1999; pp. 451-458.

Craig W. Siders et al.; "Multipulse Interferometric Frequency-Resolved Optical Gating"; IEEE Journal of Quantum Electronics, vol. 35, No. 4, Apr. 1999; pp. 432-440.

Atsushi Yabushita et al.; "SHG FROG and XFROG methods for phase/intensity characterization of pulses propagated through an absorptive optical medium"; Optics Communications; Oct. 15, 2001; pp. 227-232.

Roger G.M.P. Koumans et al.; "Time-Resolved Optical Gating Based on Dispersive Propagation: A New Method to Characterize Optical Pulses"; IEEE Journal of Quantum Electronics, vol. 36, No. 2, Feb. 2000; pp. 137-144.

Daniel J. Kane et al.; "Convergence test for inversion of frequency-resolved optical gating spectrograms"; Optics Letters, vol. 25, No. 16, Aug. 15, 2000; pp. 1216-1218.

Julie A. Gruetzmacher et al.; "Time and Frequency-Gated FID: a New Approach to Study the Vibrational Dephasing of Water"; Ultrafast Phenomena XII, 66; pp. 530-532.

Juan L.A. Chilla et al.; "Analysis of a Method of Phase Measurement of Ultrashort Pulses in the Frequency Domain"; IEEE Journal of Quantum Electronics, vol. 27, No. 5, May 1991; pp. 1228-1235.

David N. Fittinghoff et al.; "Noise sensitivity in frequency-resolved optical-gating measurements of ultrashort pulses"; J. Opt. Soc. Am. B, vol. 12, No. 10, Oct. 1995; pp. 1955-1967.

Noriaki Tsurumachi et al.; "Interferometric observation of femtosecond free induction decay"; Optics Letters, vol. 19, No. 22, Nov. 15, 1994; pp. 1867-1869.

C. Dorrer et al.; "Characterization of chirped-pulse amplification systems with spectral phase interferometry for direct electric-field reconstruction"; Applied Physics B 70 (Suppl.), 2000; pp. S77-S84.

C. Radzewicz et al.; "A poor man's FROG"; Optics Communications, Dec. 15, 2000; pp. 329-333.

C. Dorrer et al.; "Spatio-temporal characterization of the electric field of ultrashort optical pulses using two-dimensional shearing interferometry"; Applied Physics B74 (Suppl.), 2002; pp. S209-S217.

K.H. Hong et al.; "Time-frequency analysis of chirped femtosecond pulses using Wigner distribution function"; Applied Physics B74 (Suppl), 2002; pp. S231-S236.

Christophe Dorrer et al.; "Accuracy criterion for ultrashort pulse characterization techniques: application to spectral phase interferometry for direct electric field reconstruction"; Appl. Phys. B 74, vol. 19, No. 5, May 2002 ; pp. 1019-1029.

Kazunori Naganuma et al; "General Method for Ultrashort Light Pulse Chirp Measurement"; IEEE Journal of Quantum Electronics, vol. 25, No. 5; Jun. 1989; pp. 1225-1233.

Y. Ding et al.; "Time-Domain Image Processing Using Dynamic Holography"; IEEE Journal of Selected Topics in Quantum Electronics, vol. 4, No. 2; Mar./Apr. 1998; pp. 332-341.

Chris Iaconis et al; "Self-Referencing Spectral Interferometry for Measuring Ultrashort Optical Pulses"; IEEE Journal of Quantum Electronics, vol. 35, No. 4; Apr. 1999; pp. 501-509.

Jung-Ho Chung et al.; "Ambiguity of Ultrashort Pulse Shapes Retrieved From the Intensity Autocorrelation and the Power Spectrum"; IEEE Journal on Selected Topics of Quantum Electronics, vol. 7, No. 4; Jul./Aug. 2001; pp. 656-666.

V. Kabelka et al.; "Time-frequency imaging of a single ultrashort light pulse from anularly resolved autocorrelation"; Optics Letters, vol. 20, No. 1; Jun. 1, 1995; pp. 1301-1303.

June-Koo Rhee et al.; "Real-time dispersion analyzer of femtosecond laser pulses with use of a spectrally and temporally resolved upconversion technique"; J. Opt. Soc. Am. B, vol. 13, No. 8; Aug. 1996; pp. 1780-1785.

(56) References Cited

OTHER PUBLICATIONS

Marco A. Krumbugel et al.; "Direct ultrashort-pulse intensity and phase retrieval by frequency-resolved optical gating and a computational neural network"; Optics Letters, vol. 21, No. 2; Jan. 15, 1996; pp. 143-145.

David N. Fittinghoff et al.; "Measurement of the intensity and phase of ultraweak, ultrashort laser pulses"; Optics Letters, vol. 21, No. 12; Jun. 15, 1996; pp. 884-886.

T. Feurer et al.; "Measuring the temporal intensity of ultrashort laser pulses by triple correlation"; Appl. Phys. B; 1998; pp. 163-168.

Alfred Kwok et al.; "Frequency-Resolved Optical Gating Using Cascaded Second-Order Nonlinearities"; Journal of Selected Topics in Quantum Electronics, vol. 4, No. 2; Mar./Apr. 1998; pp. 271-277.

Daniel J. Kane; "Real-Time Measurement of Ultrashort Laser Pulse Using Principal Component Generalized Projection"; IEEE Journal of Selected Topics in Quantum Electronics; vol. 4, No. 2; Mar./Apr. 1998; pp. 278-284.

Scott A. Diddams et al.; "Characterizing the Nonlinear Propagation of Femtosecond Pulses in Bulk Media"; IEEE Journal of Selected Topics in Quantum Electronics, vol. 4, No. 2; Mar./Apr. 1998; pp. 306-316.

Michael J. Stimson et al.; "Noisy-light correlation functions by frequency resolved optical gating"; J. Opt. Soc. Am. B, vol. 15, No. 2; Feb. 1998; pp. 505-514.

J. W. Nicholson et al.; "Full-field characterization of femtosecond pulses by spectrum and cross-correlation measurements"; Optics Letters, vol. 24, No. 23; Dec. 1, 1999; pp. 1774-1776.

F. Romstad et al.; "Measurement of Pulse Amplitude and Phase Distortion in a Semiconductor Optical Amplifier: from Pulse Compression to Breakup"; IEEE Photonics Technology Letters, vol. 12, No. 12; Dec. 2000; pp. 1674-1676.

Tzu-Ming Liu et al.; "Triple-optical autocorrelation for direct optical pulse-shape measurement"; Applied Physics Letters, vol. 81, No. 8; Aug. 19, 2002; pp. 1402-1404.

Yoshihiro Takagi et al.; "Multiple- and single-shot autocorrelator based on two-photon conductivity in semiconductors"; Optics Letters, vol. 17, No. 9; May 1, 1992; pp. 658-660.

Thomas J. Dunn et al.; "Experimental Determination of the Dynamics of a Molecular Nuclear Wave Packet via the Spectra of Spontaneous Emission"; Physical Review Letters, vol. 70, No. 22; May 31, 1993; pp. 3388-3391.

A.N. Naumov et al.; "Frequency-time and time-space mappings for single-shot coherent four-wave mixing with chirped pulses and broad beams"; Journal of Raman Spectroscopy, 2001; pp. 960-970.

E.T.J. Nibbering et al.; "Spectral determination of the amplitude and the phase of intense ultrashort optical pulses"; J. Opt. Soc. Am. B, vol. 13, No. 2; Feb. 1996; pp. 317-329.

Victor Wong et al.; "Ultrashort-pulse characterization from dynamic spectrograms by iterative phase retrieval"; J. Opt. Soc. Am. B, vol. 14, No. 4; Apr. 1997; pp. 944-949.

Sarah M. Gallagher et al.; "Heterodyne detection of the complete electric field of femtosecond four-wave mixing signals"; J. Opt. Soc. Am. B, vol. 15, No. 8; Aug. 1998; pp. 2338-2345.

C. Dorrer et al.; "Single-shot real-time characterization of chirped-pulse amplification systems by spectral phase interferometry for direct electric-field reconstruction"; Optics Letters, vol. 24, No. 22; Nov. 15, 1999; pp. 1644-1646.

C. Dorrer; "Implementation of spectral phase interferometry for direct electric-field reconstruction with a simultaneously recorded reference interferogram"; Optics Letters, vol. 24, No. 21; Nov. 1, 1999; pp. 1532-1534.

C.Y. Chien et al.; "Single-shot chirped-pulse spectral interferometry used to measure the femtosecond ionization dynamics of air"; Optics Letters, vol. 25, No. 8; Apr. 15, 2000; pp. 578-580.

J.W. Nicholson et al.; "Unbalanced third-order correlations for full characterization of femtosecond pulses"; Optics Letters, vol. 25, No. 24; Dec. 15, 2000; pp. 1801-1803.

J. M. Dudley, et al.; "Direct measurement of pusle distortion near the zero-disperson wavelength in an optical fiber by frequency-resolved optical gating"; Optics Letters, vol. 22, No. 7; Apr. 1, 1997; 457-459.

M.C. Chen et al.; "Freezing phase scheme for fast adaptive control and its application to characterization of femtosecond coherent optical pulses reflected from semiconductor saturable absorber mirrors"; J. Opt. Soc. Am. B, vol. 22, No. 5; May 2005; pp. 1134-1142.

I. Amat-Roldan et al.; "Measurement of electric field by interferometric spectral trace observation"; Optics Letters, vol. 30, No. 9; May 1, 2005; pp. 1063-1065.

I. Amat-Roldan et al.; "Starch-based second-harmonic-generated colinear frequency-resolved optical gating pulse characterization at the focal plane of a high-numerical-aperture lens"; Optics Letters, vol. 29, No. 19; Oct. 1, 2004; pp. 2282-2284.

Gregory D. Goodno et al.; "Ultrafast heterodyne-detected transient-grating spectroscopy using diffractive optics"; Optical Society of America, vol. 15, No. 6, Jun. 1998; pp. 1791-1794.

L. Misoguti et al.; "Generation of Broadband VUV Light Using Third-Order Cascaded Processes"; Physical Review Letters, vol. 87, No. 1, Jul. 2, 2001; pp. 013601-1-013601-4.

D. Zeidler et al.; "Amplification of tailored white-light continuum"; Applied Physics, B74 (Suppl), 2002; pp. S51-S56.

T. Brixner et al.; "Generation and characterization of polarization-shaped femtosecond laser pulses"; Applied Physics B74 (Suppl), 2002; pp. S133-S144.

Jeffrey L. Krause et al.; "Creating and Detecting Shaped Rydberg Wave Packets"; Physical Review Letters, vol. 79, No. 25; Dec. 22, 1997; pp. 4978-4981.

S. Backus et al.; "16-fs, 1-µ J ultraviolet pulses generated by third-harmonic conversion in air"; Optics Letters, vol. 21, No. 9; May 1, 1996; pp. 665-667.

Julie A. Gruetzmacher et al.; "Few-cycle mid-infrared pulse generation, characterization and coherent propagation in optically dense media"; Review of Scientific Instruments, vol. 73, No. 6; Jun. 2002; pp. 2227-2236.

T. Kobayashi et al.; "Tunable visible and near-infrared pulse generator in a 5 fs regime"; Appl. Phys. B 70 (Suppl); 2000; pp. S239-S246.

A. Poppe et al; "Few-cycle optical waveform synthesis"; Applied Physics B 72; 2001; pp. 373-376.

Peifang Tian et al.; "Ultrafast measurement of two-photon absorption by loss modulation"; Optics Letters, vol. 27, No. 18; Sep. 15, 2002; pp. 1634-1636.

M. Hentschel et al.; "Generation of 0.1-TW optical pulses with a single-stage Ti:sapphire amplifier at a 1-kHz repetition rate"; Appl. Phys. B 70 [Suppl.]; 2000; pp. S161-S164.

Photogen Technologies, Inc., "Photogen-Technology"; www.photogen.com/body/tech_body.html; Dec. 20, 2001 (19 pages).

W.M. Sharman et al.; "Photodynamic therapeutics: basic principles and clinical applications"; DDT, vol. 4, No. 11; Nov. 1991; pp. 507-517.

Allison Albrecht Ferro et al.; "Complete femtosecond linear free induction decay, Fourier algorithm for dispersion relations and accuracy of the rotating wave approximation"; Journal of Chemical Physics, vol. 114, No. 10; Mar. 8, 2001; pp. 4649-4656.

J.P. Ogilvie et al.; "Fourier transform measurement of two-photon excitation spectra: applications to microscopy and optimal control"; Optics Letters, vol. 30, No. 8; Apr. 15, 2005; pp. 911-913.

D. Lalovic et al.; "Quantum mechanics in terms of non-negative smoothed Wigner functions"; Physical Review A, vol. 46, No. 3; Aug. 1, 1992; pp. 1206-1212.

Christopher J. Bardeen et al.; "Using time-dependent rate equations to describe chirped pulse excitation in condensed phases"; Chemical Physics Letters 302; 1999; pp. 405-410.

Yu-Chen Shen et al.; "What can short-pulse pump-probe spectroscopy tell us about Franck-Condon dynamics?"; Journal of Chemical Physics, vol. 110. No. 20; May 22, 1999; pp. 9793-9806.

M. Ovchinnikov et al.; "Semiclassical molecular dynamics computation of spontaneous light emission in the condensed phase: Resonance Raman spectra"; Journal of Chemical Physics, vol. 114, No. 16; Apr. 22, 2001; pp. 7130-7143.

S. Yeremenko et al.; "The criterion of pulse reconstruction quality based on Wigner representation"; Applied Physics B 70 (Suppl); 2000; pp. S109-S117.

David C. Clary; "Quantum Theory of Chemical Reaction Dynamics"; Science, vol. 279, Mar. 20 1998; p. 1879.

(56) References Cited

OTHER PUBLICATIONS

B.D. Fainberg; "Diagram Technique for Nonlinear Optical Spectroscopy in the Fast Electronic Dephasing Limit"; Journal of the Chinese Chemical Society, 47; 2000; pp. 579-582.
Chantal Daniel et al.; "Deciphering the Reaction Dynamics Underlying Optimal Control Laser Fields"; Science Magazine, vol. 299; Jan. 24, 2003; pp. 536-539.
T. Witte et al.; "Controlling molecular ground-state dissociation by optimizing vibrational ladder climbing"; Journal of Chemical Physics, vol. 118, No. 5; Feb. 1, 2003; pp. 2021-2024.
R.J. Levis et al.; "Closing the Loop on Bond Selective Chemistry Using Tailored Strong Field Laser Pulses"; the Journal of Physical Chemistry, vol. 106, No. 27; Jul. 11, 2002; pp. 6427-6444.
Mustafa Demirplak et al.; "Optical control of molecular dynamics in a liquid"; Journal of Chemical Physics, vol. 116, No. 18; May 8, 2002; pp. 8028-8035.
M. Bergt et al.; "Time-resolved organometallic photochemistry Femtosecond fragmentation and adaptive control of CpFe(CO)2X (X=Cl,Br,I)"; Journal of Organometallic Chemistry 661; 2002; pp. 199-209.
Ben R. Torralva et al; "Mechanisms for laser control of chemical reactions"; Journal of Modern Optics, vol. 49, No. 3/4; 2002; pp. 593-625.
N.H. Damrauer et al.; "Control of bond-selective photochemistry in CH2BrCl using adaptive femtosecond pulse shaping"; The European Physical Journal D, 20, 2002; pp. 71-76.
L. Windhorn et al.; "Molecular dissociation by mid-Ir femtosecond pulses"; Chemical Physics Letters 357, May 3, 2002; pp. 85-90.
Robert J. Levis et al.; "Selective Bond Dissociation and Rearrangement with Optimally Tailored, Strong-Field Laser Pulses"; Science Magazine, vol. 292; Apr. 27, 2001; pp. 709-713.
T. Brixner et al.; "Problem complexity in femtosecond quantum control"; Chemical Physics 267; 2001; pp. 241-246.
O.M. Sarkisov et al.; "Control of elementary chemical reactions by femtosecond light pulses"; Quantum Electronics, vol. 31, No. 6; 2001; pp. 483-488.
Julie A. Mueller et al.; "Competing isomeric product channels in the 193 nm photodissociation of 2-chloropropene and in the unimolecular dissociation of the 2-propenyl radical"; Journal of Chemical Physics, vol. 114, No. 10; Mar. 8, 2001; pp. 4505-4521.
Chantal Daniel et al.; "Analysis and control of laser induced fragmentation processes in CpMn(CO)3"; Chemical Physics 267; 2001; pp. 247-260.
A. Glass et al.; "Control of the photodissociation of CsCl"; Applied Physics B 71; 2000; pp. 267-276.
T. Frohnmeyer et al.; "Femtosecond pump-probe photoelectron spectroscopy on Na2: a tool to study basic coherent control schemes"; Applied Physics B 71; 2000; pp. 259-266.
M. Bergt et al.; "Controlling the Femtochemistry of Fe(CO)5"; J. Phys. Chem. A, vol. 103, No. 49; 1999; pp. 10381-10387.
A. Assion et al.; "Coherent control by a single phase shaped femtosecond laser pulse"; Chemical Physics Letters 259; Sep. 13, 1996; pp. 488-494.
Langchi Zhu et al.; "Coherent Laser Control of the Product Distribution Obtained in the Photoexcitation of HI"; Science Magazine, vol. 270; Oct. 6, 1995; pp. 77-80.
Yu-hui Chiu et al.; "Vibrational mode effects, scattering dynamics and energy disposal in reaction of C2H2 with methane"; J. Chem. Phys., vol. 102, No. 3; Jan. 15, 1995; pp. 1199-1216.
J.S. Keller et al.; "Selective bond fission in methyl mercaptan at 193 nm via radial derivative coupling between the 21A" and 11A" adiabatic electronic states"; J. Chem. Phys. vol. 96, No. 6; Mar. 15, 1992; pp. 4324-4329.
I. Bar et al.; "Mode-selective bond fission: Comparison between the photodissociation of HOD (0,0,1) and HOD (1,0,0)"; J. Chem. Phys. vol. 95, No. 5; Sep. 1, 1991; pp. 3341-3346.
Michael J. Bronikowski et al.; "Bond-specific chemistry: OD:OH product ratios for the reactions H+HOD(100) and H+HOD(001)"; J. Chem. Phys., vol. 95, No. 11; Dec. 1, 1991; pp. 8647-8648.

I. Bar et al.; "Direct observation of preferential bond fission by excitation of a vibrational fundamental: Photodissociation of HOD (0,0,1)"; J. Chem. Phys., vol. 93, No. 3; Aug. 1, 1990; pp. 2146-2148.
R.L. VanderWal et al.; "Selectively breaking the O-H bond in HOD"; J. Chem. Phys., vol. 92, No. 1; Jan. 1, 1990; pp. 803-805.
Neil Shafer et al.; "Isotope effect in the photodissociation of HDO at 157.5 nm"; J. Chem. Phys., vol. 90, No. 11; Jun. 1, 1989; pp. 6807-6808.
L.J. Butler et al.; "The electronic state-selective photodissociation of CH2BrI at 248, 210 and 193 nm"; J. Chem. Phys. vol. 86, No. 4; Feb. 15, 1997; pp. 2051-2074.
L.J. Butler et al.; "Bond selective photochemistry in CH2BrI through electronic excitation at 210 nm"; J. Chem. Phys., vol. 84, No. 7; Apr. 1, 1986; pp. 4104-4106.
David J. Tannor et al.; "Control of selectivity of chemical reaction via control of wave packet evolution"; J. Chem. Phys., vol. 83, No. 10; Nov. 15, 1985; pp. 5013-5018.
Christopher J. Bardeen et al.; "Quantum Control of NaI Photodissociation Reaction Product States by Ultrafast Tailored Light Pulses"; J. Phys. Chem. A, vol. 101, No. 20; 1997; pp. 3815-3822.
V.A. Apkarian; 'Comment on "Time-resolved laser induced harpoon reactions"'; J. Chem. Phys. vol. 106, No. 12; Mar. 22, 1997; pp. 5298-5299.
R.B. Vrijen et al.; "Limitations on quantum ladder climbing in complex systems"; Physical Review A, vol. 56, No. 3; Sep. 1997; pp. 2205-2212.
Lutfur R. Khundkar et al.; "Ultrafast Molecular Reaction Dynamics in Real-Time: Progress Over a Decade"; Annu. Rev. Phys. Chem., 1990; pp. 15-60.
Stuart A. Rice; "Optical control of reactions"; Nature magazine, vol. 403; Feb. 3, 2000; pp. 496-497.
Richard N. Zare; "Laser Control of Chemical Reactions"; Science magazine, vol. 279; Mar. 20, 1998; pp. 1875-1879.
Stuart A. Rice; "Active Control of Molecular Dynamics: Coherence versus Chaos"; Journal of Statistical Physics, vol. 101, Nos. 1/2; 2000; pp. 187-212.
Herschel Rabitz et al.; "Whither the Future of Controlling Quantum Phenomena?"; Science magazine, vol. 288; May 5, 2000; pp. 824-828.
Yuri T. Mazurenko; "Spectral Holography and Spectral Nonlinear Optics of Ultrashort Pulses"; Journal of the Chinese Chemical Society, vol. 47, No. 4A; 2000; pp. 679-683.
Marcos Dantus; "Coherent Nonlinear Spectroscopy: From Femtosecond Dynamics to Control"; Annu. Rev. Phys. Chem. 2001; pp. 639-679, C1-C7.
Stuart A. Rice; "Interfering for the good of a chemical reaction"; Nature magazine; vol. 409; Jan. 18, 2001; pp. 422-426.
Wolfgang Kiefer et al.; "Femtosecond time-resolved spectroscopy of elementary molecular dynamics"; Naturwissenschaften; 2002; pp. 250-258.
Alois Renn et al.; "Multidimensional Holography by Persistent Spectral Hole Burning"; The Journal of Physical Chemistry A, vol. 106, No. 13; Apr. 4, 2002; pp. 3045-3060.
T.C. Weinacht et al.; "Using feedback for coherent control of quantum systems"; Journal of Optics B: Quantum and Semiclassical Optics; 2002; pP. R35-R52.
Niels E. Henriksen; "Laser control of chemical reactions"; Chem. Soc. Rev. 3137 42; 2002; pp. 37-42.
Stuart A. Rice et al.; "Active control of product selection in a chemical reaction: a view of the current scene"; Phys. Chem. Chem. Phys.; 2002; pp. 1683-1700.
Allen J. Bard et al.; "Holy Grails in Chemistry"; American Chemical Society, vol. 28, No. 3; Mar. 1995.
Marcos Dantus; "Ultrafast Probing and Control of Molecular Dynamics: Beyond the Pump-Probe Method"; pp. 169-188. Kuhn & Weyh SRZ Sep. 4, 2001.
Bern Kohler et al.; "Controlling the Future of Matter"; Acc. Chem. Res., vol. 28, No. 3; 1995; pp. 133-140.
M.R. Fetterman et al.; "Propagation of Complex Laser Pulses in Optically Dense Media"; The American Physical Society, Physical Review Letters, vol. 82, No. 20, May 17, 1999, pp. 3984-3987,
D. Yelin et al.; "Adaptive femtosecond pulse compression"; Optics Letters, vol. 22, No. 23, Dec. 1, 1997; pp. 1793-1795.

(56) References Cited

OTHER PUBLICATIONS

A.V. Sokolov; "Subfemtosecond compression of periodic laser pulses"; Optics Letters, vol. 24, No. 17, Sep. 1, 1999; pp. 1248-1250.

H.S. Eisenberg et al.; "Phase Defects in Self-Focusing of Ultrashort Pulses"; Physical Review Letters, vol. 83, No. 3, Jul. 19, 1999; pp. 540-543.

D.M. Villeneuve et al.; "Using frequency-domain manipulation of stretched femtosecond laser pulses to create fast rise and fall times on picosecond pulses"; Applied Physics B74 (Suppl), 2002; pp. S157-S161.

Dai-Sik Kim et al.; "Femtosecond-pulse distortion in quantum wells"; Appl. Phys B 74, vol. 48. No. 24; Dec. 15, 1993; pp. 17902-17905.

Anthony P. Peirce et al.; "Optimal control of quantum-mechanical systems: Existence, numerical approximation and applications"; Physical Review A, vol. 37, No. 12; Jun. 15, 1988; pp. 4950-4964.

J.M. Geremia et al.; "Incorporating physical implementation concerns into closed loop quantum control experiments"; Journal of Chemical Physics, vol. 13, No. 24; Dec. 22, 2000; pp. 10841-10848.

Thomas Hornung et al.; "Teaching optimal control theory to distill robust pulses even under experimental constraints"; Physical Review A, vol. 65; 2002; pp. 021403-1-021403-4.

Jianshu Cao et al.; "Intrapulse Dynamical Effects in Multiphoton Processes: Theoretical Analysis"; J. Phys. Chem. A; vol. 102, 1998; pp. 4284-4290.

Amichay Vardi et al.; "Laser catalysis with pulses"; Physical Review A, vol. 58, No. 2; Aug. 1998; pp. 1352-1360.

Kazuya Takasago et al.; "Evaluation of Femtosecond Pulse Shaping with Low-Loss Phase-Only Masks"; IEEE Journal of Selected Topics in Quantum Electronics, vol. 4, No. 2; Mar./Apr. 1998; pp. 346-352.

M.E. Fermann et al.; "Shaping of ultrashort optical pulses by using an integrated acousto-optic tunable filter"; Optics Letters, vol. 18, No. 18; Sep. 15, 1993; pp. 1505-1507.

V.L. da Silva et al.; "Nonlinear pulse shaping and causality"; Optics Letters, vol. 18, No. 8; Apr. 15, 1993; pp. 580-582.

E. Zeek et al.; "Adaptive pulse compression for transform-limited 15-fs high-energy pulse generation"; Optics Letters, vol. 25, No. 8; Apr. 15, 2000; pp. 587-589.

A. Apolonski et al.; "Controlling the Phase Evolution of Few-Cycle Light Pulses"; Physical Review Letters, vol. 85, No. 4; Jul. 24, 2000; pp. 740-743.

Christophe Dorrer et al.; "Phase Amplitude Coupling in Spectral Phase Modulation"; IEEE Journal of Selected Topics in Quantum Electronics, vol. 4, No. 2; Mar./Apr. 1998; pp. 342-345.

David J. Jones et al.; "Carrier-Envelope Phase Control of Femtosecond Mode-Locked Lasers and Direct Optical Frequency Synthesis"; Science magazine, vol. 288; Apr. 28, 2000; pp. 635-639.

Vladimir Kalosha et al.; "Generation of Single Dispersion Precompensated 1-fs Pulses by Shaped-Pulse Optimized High-Order Stimulated Raman Scattering"; Physical Review Letters, vol. 88, No. 10; Mar. 11, 2002; pgs. 103901-1-13901-4.

Donna Strickland et al.; "Compression of Amplified Chirped Optical Pulses"; Optics Communications; vol. 55, No. 6; Oct. 15 1985; pp. 447-449.

H. Wang et al.; "Abstract-20-fs pulse shaping with a 512-element phase-only liquid crystal modulator"; IEEE Journal of Selected Topics in Quantum Electronics; 7 (4): 718-727; Jul./Aug. 2001 (1 page).

L. Xu et al.; "Abstract-Programmable chirp compensation for 6-fs pulse generation with a prism-pair-formed pulse shaper"; IEEE Journal of Quantum Electronics; 36 (8): 893-899; Aug. 2000 (1 page).

CVI Laser Corporation; "TNM-2 Negative Group Velocity Dispersion Mirrors"; www.cvilaser.com/ultra-fast; Jan. 13, 2002 (2 pages).

H. Takada et al.; "Large-ratio stretch and recompression of sub-10-fs pulses utilizing dispersion managed devices and a spatial light modulator"; Appl. Phys. B 74 [Suppl.]; 2002; pp. S253-S257.

N. Karasawa et al.; "Optical pulse compression to 5.0 fs by by use only a spatial light modulator for phase compensation"; J. Opt. Soc. Am. B, vol. 18, No. 11; Nov. 2001; pp. 1742-1746.

C.P.J. Barty et al.; "Generation of 18-fs, multiiterawatt pulses by regenerative pulse shaping and chirped-pulse amplification"; Optics Letters, vol. 21, No. 9; May 1, 1996; pp. 668-670.

Marcos Dantus; GeneticAlgorithm-v4.nb to simulate an adaptive genetic algorithm;Oct. 2001; pp. 1-7.

M. Hacker et al.; "Iterative Fourier transform algorithm for phase-only pulse shaping"; ' Optics Express, vol. 9, No. 4, Aug. 13, 2001; pp. 191-199.

T. Brixner et al.; "Feedback-controlled optimization of amplified femtosecond laser pulses"; Applied Physics B 68; 1999; pp. 281-284.

A. Efimov et al.; "Minimization of dispersion in an ultrafast chirped pulse amplifier using adaptive learning"; Appl. Phys. B 70 (Suppl); 2000; pp. S133-S141.

D. Zeidler et al.; "Evolutionary algorithms and their application to optimal control studies"; Physical Review A, vol. 64; 2001; pp. 023420-1-023420-13.

C. Rangan et al.; "Optimally shaped terahertz pulses for phase retrieval in a Rydberg-atom data register"; Physical Review A, vol. 64; 2001; pp. 033417-1-033417-5.

T. Tanabe et al.; "Compensation for a Transfer Function of a Regenerative Amplifier to Generate Accurately Shaped Ultrashort Pulses in Both the Amplitude and Phase"; IEE J. of Selected Topics in QUantum Elecronics, vol. 10, No. 1; Jan./Feb. 2004; pp. 221-228.

Hosseini, S. Abbas et al.; "Coherent control of multiphoton transitions with femtosecond pulse shaping"; Physical Review A; pp. 033410-1-033410-7.

Yan, Y.J. et al.; "Electronic dephasing, vibrational relaxation, and solvent friction in molecular nonlinear optical line shapes"; J. Chems. Phys.; Oct. 15, 1988; pp. 5160-5176.

Meshulach, M. et al.; "Coherent quantum control of multiphoton transitions by shaped ultrashort optical pulses" Phys. Rev. A 60; 1999; pp. 1287-1292.

Weinacht, T.C. et al.; "Controlling the shape of a quantum wavefunction"; Nature, vol. 397; Jan. 1999; pp. 233-235.

Buist, A.H. et al.; "Probing microscopic chemical environments with high-intensity chirped pulses"; Optics Letters 24; 1999; pp. 244-246.

Broers, B. et al.; "Large interference effects of small chirp observed in two-photon absorbtion"; Opt. Commun. 91; 1992; p. 57-61.

Broers, B. et al.; "Diffraction and focusing of spectral energy in multiphoton processes"; Phys Rev. A 46; 1992; p. 2749-2756.

Walowicz, K.A. et al.; "Multiphoton Intrapulse Interference 1: Control of Multiphoton Processes in Condensed Phases"; J. Phys. Chem A 106 (41); Oct. 17, 2002; pp. 9369-9373.

Zheng, Z. et al.; "Coherent control of second harmonic generation using spectrally phase coded femtosecond waveforms"; Chem. Phys. 267; 2001; pp. 161-171.

Clara et al.; "Femtoscond laser mass spectroscopy of ferrocenes: Photochemical stabilization by bridged cyclopentadienyl rings?"; International Journal of Mass Spectrometry, Elsevier Science Publishers, vol. 203, No. 1-3; Dec. 26, 2000; pp. 71-81.

Bucksbaum, Philip; "An atomic dimmer switch"; Nature; Nov. 19, 1998; vol. 396; pp. 217-219.

Dela Cruz, J.M. et al.; "Multiphoton Intrapulse Interference 3: Probing Microscopic Chemical Environments"; J. Phys. Chem. A 2004, 108; pp. 53-58.

Goswami, D.; "Optical pulse shaping approaches to coherent control"; Physics Reports 374; 2004; pp. 385-481.

Leibfried, D. et al.; "Quantum information with trapped ions at NIST"; Journal of Modern Optics; vol. 50, No. 6/7; Apr.-May 2003; pp. 1115-1129.

Lozovoy, V.V.; "Multiphoton intrapulse interference. II. Control of two- and three-photon laser induced flurorescence with shaped pulses"; J. Chem. Phys. 118 (7); Feb. 15, 2005; pp. 3187-3196.

Roy, I. et al; "Ceramic-based nanoparticles entrapping water-soluble photosensitizing drugs: A novel drug carrier system for photodynamic therapy"; J. Am. Chem. Soc. 125; 2003, pp. 7860-7865.

VandenBout, D.A. et al.; "Discrete intensity jumps and intramolecular electronic energy transfer in the spectroscopy of single conjugated polymer molecules"; Science 277; 1997; pp. 1074-1077.

(56) References Cited

OTHER PUBLICATIONS

Paye, J.; "How to Measure the Amplitude and Phase of an Ultrashort Light Pulse with an Autocorrelator and a Spectrometer"; IEEE Journal of Quantum Electronics, vol. 30, No. 11; Nov. 1994; pp. 2693-2697.
Kovtoun et al.; "Mass-Correlated Pulsed Extraction: Theoretical Analysis and Implementation With a Linear matrix-Assisted laser Desorption/Ionization Time of Flight Mass Spectrometer"; Journal of the American Society for Mass Spectrometry, Elsevier Science Inc; vol. 11, No. 10; Oct. 2000; pp. 841-853.
Cumpston, B.H. et al.; "New Photopolymers based on Two-Photon Absorbing Chromophores and Application to Three-Dimensional Microfabricaton and Optical Storage"; Mat. Res. Soc. Symp. Proc; vol. 488; 1998; pp. 217-225.
Cumpston, B.H. et al.; "Two-photon polymerization initiators for three-dimensional optical data storage and microfabrication"; Letters to Nature; vol. 398; Mar. 4, 1999; pp. 51-54.
Lu, Y.M. et al.; "Highly sensitive two-photon chromophores applied to three dimensional lithographic microfabrication: design, synthesis and characterization towards two-photon absorbtion cross section"; J. Mater Chem. 14(1); 2004; pp. 75-80.
Postnikova, B.J. et al.; "Towards nanoscale three-dimensional fabrication using two-photon initiated polymerization and near-field excitation"; Microelectron. Eng. 69 (2-4); Sep. 2003; pp. 459-465.
Sun, H.B. et al.; "Two-photon laser precision microfabrication and its applications to micronano devices and systems"; J. Lightwave Technol. 21(3); Mar. 2003; pp. 624-633.
Mitra et al.; "Nonlinear Limits to the Information Capacity of Optical Fibre Communications"; Nature; vol. 411; Jun. 28, 2001; pp. 1027-1030.
Brattke, S. et al.; "Generation of Photon Number States on Demand via Cavity Quantum Electrodynamics"; Phys. Rev. Lett.; vol. 86; Apr. 16, 2001; pp. 3534-3537.
Goswami, D.; "Ultrafast Pulse Shaping Approaches to Quantum Computing"; Indian Institute of Technology; Dec. 24, 2003 (8 pages).
Xu, C. et al.; "Two photon optical beam induced current imaging throughout backside of integrated circuits"; Appl. Phys. Lett. 71; 1997; pp. 2578-2580.
Yang, W. et al.; "High-ratio Electro-optical Data Compression for Massive Accessing Networks Using AOM-based Ultrafast Pulse Shaping"; Journal of Optical Communications; vol. 22, No. 1; 2001; pp. 694-697.
Kane, Daniel J. et al.; "Single-shot measurement of the intensity and phase of an arbitrary ultrashort pulse by using frequency-resolved optical gating"; Optics Letters, vol. 18, No. 10; May 15, 1993; pp. 823-825.
Kane, Daniel J. et al.; "Single-shot measurement of the intensity and phase of a femtosecond UV laser pulse with frequency-resolved optical gating"; Optics Letters, vol. 19, No. 14; Jul. 15, 1994; pp. 1061-1063.
Clement, Tracy Sharp et al.; "Single-Shot measurement of the amplitude and phase of ultrashort laser pulses in the violet"; Optics Letters, vol. 20, No. 1; Jan. 1, 1995; pp. 70-72.
Kohler, Bern et al.; "Phase and intensity characterization of femtosecond pulses from a chirped-pulse amplifier by frequency-resolved optical gating"; Optics Letters, vol. 20, No. 5; Mar. 1, 1995; pp. 483-485.
Sweetser, John N. et al.; "Transient-grating frequency-resolved optical gating"; Optics Letters, vol. 22, No. 8; Apr. 15, 1997; pp. 519-521.
Trebino, Rick et al.; "Measuring ultrashort laser pulses in the time-frequency domain using frequency-resolved optical gating"; Rev. Sci. Instrum. 68 (9); Sep. 1997; pp. 3277-3295.
Dudley, John M. et al.; "Complete Characterization of Ultrashort Pulse Sources at 1550 nm"; IEEE Journal of Quantum Electronics, vol. 35, No. 4; Apr. 1999; pp. 441-450.
Trebino, Rick et al.; "The Dilemma of Ultrashort-Laser-Pulse Intensity and Phase Measurement and Applications"; IEEE Journal of Quantum Electronics, vol. 35, No. 4; Apr. 1999; pp. 418-420.
Cormack, I.G. et al.; "Practical measurement of femtosecond optical pulses using time-resolved optical gating"; Optics Communications 194; Jul. 15, 2001; pp. 415-424.
Chu, K.C. et al.; "Direct measurement of the spectral phase of femtosecond pulses"; Optics Letters, vol. 20, No. 8; Apr. 15, 1995; pp. 904-906.
Sullivan, A. et al.; "Quantitative investigation of optical phase-measuring techniques for ultrashort pulse lasers"; J. Opt. Soc. Am. B, vol. 13, No. 9; Sep. 1996; pp. 1965-1978.
Baltuska, Andrius et al.; "Amplitude and phase characterization of 4.5-fs pulses by frequency-resolved optical gating"; Optics Letters, vol. 23, No. 18; Sep. 15, 1998; pp. 1474-1476.
Gallmann, L. et al.; "Techniques for the characterization of sub-10-fs optical pulses: a comparision"; Appl. Phys. B 70 (Suppl): 2000; pp. S67-S75.
Anderson, M.E. et al; "The effects of noise on ultrashort-optical-pulse measurement using SPIDER"; Appl. Phys. B 70 (Suppl); 2000; pp. S85-S93.
Nicholson, J.W. et al; "Noise sensitivity and accuracy of femtosecond pulse retrieval by phase and intensity from correlation and spectrum only (PICASO)"; J. Opt. Soc. Am. B; vol. 19, No. 2; Feb. 2002; pp. 330-339.
Dorrer, Christophe et al.; "Precision and consistency criteria in spectral phase interferometry for direct electric-field reconstruction"; J. Opt. Soc. Am. B, vol. 19, No. 5; May 2002; pp. 1030-1038.
Walmsley, Ian A. et al.; "Characterization of the electric field of ultrashort optical pulses"; J. Opt. Soc. Am. B., vol. 13, No. 11; Nov. 1996; pp. 2453-2463.
Lange, H. Rudiger et al.; "Reconstruction of the Time Profile of Femtosecond Laser Pulses through Cross-Phase Modulation"; IEEE Journal of Selected Topics in Quantum Electronics, vol. 4, No. 2; Mar./Apr. 1998; pp. 295-300.
Iaconis, C. et al.; "Direct Interferometric Techniques for Characterizing Ultrashort Optical Pulses"; IEEE Journal of Selected Topics in Quantum Electronics, vol. 4, No. 2; Mar./Apr. 1998; pp. 285-294.
Iaconis, C. et al.; "Spectral phase interferometry for direct electric-field reconstruction of ultrashort optical pulses"; Optics Letters, vol. 23, No. 10, May 15, 1998; pp. 792-794.
Dietrich, P. et al.; "Determining the absolute carrier phase of a few-cycle laser pulse"; Optics Letters, vol. 25, No. 1, Jan. 1, 2000; pp. 16-18.
Reid, D.T. et al.; "Amplitude and phase measurement of mid-infrared femtosecond pulses by using cross-correlation frequency-resolved optical gating"; Optics Letters, vol. 25, No. 19, Oct. 1, 2000; pp. 1478-1480.
Michelmann, K. et al.; "Measurement of the Page function of an ultrashort laser pulse"; Optics Communications; Oct. 15, 2001, pp. 163-170.
Gallmann, L. et al.; "Spatially resolved amplitude and phase characterization of femtosecond optical pulses"; Optics Letters, vol. 26, No. 2; Jan. 15, 2001; pp. 96-98.
Kakehata, Masayuki et al.; "Single-shot measurement of carrier-envelope phase changes by spectral interferometry"; Optics Letters, vol. 26, No. 18; Sep. 15, 2001; pp. 1436-1438.
Geindre, J.P. et al.; "Single-shot spectral interferometry with chirped pulses"; Optics Letters, vol. 26, No. 20; Oct. 15, 2001; pp. 1612-1614.
Dorrer, C. et al.; "Direct space-time characterization of the electric fields of ultrashort optical pulses"; Optics Letters, vol. 27, No. 7; Apr. 1, 2002; pp. 548-550.
Trebino, R. et al; "Measuring Ultrashort Laser Pulses Just Got a Lot Easier!"; Optics & Photonics News; Jun. 2001; pp. 22-25.
Zheng, Z. et al. "Spectral phase correlation of coded femtosecond pulses by second-harmonic generation in thick nonlinear crystals"; Opt. Lett. 25; 2000; pp. 984-986.
Spielmann, C. et al.; "Ultrabroadband Femtosecond Lasers"; IEEE Journal of Quantum Electronics; vol. 30, No. 4; Apr. 1994; pp. 1100-1114.
Yelin, D. et al.; "Laser scanning third-harmonic-generation microscopy in biology"; Optics Express; vol. 5, No. 8; Oct. 11, 1999; pp. 169-175.

(56) References Cited

OTHER PUBLICATIONS

Zipfel, W.R. et al; "Nonlinear magic: multiphoton microscopy in the biosciences"; Natire Biotechnology, 121 (11); Nov. 2003; pp. 1369-1377.
Larson, D.R. et al.; "Water soluble quantum dots for multiphoton imaging in vivo"; Science 300: May 30, 2003; pp. 1434-6.
Osborn, D.L. et al.; "Spectral and intensity dependence of spatially resolved two-photon conductivity defects on a GaAsP photodiode"; J. Appl. Phys 89; 2001; pp. 626-633.
Pastirk, I. et al; "Selective two-photon microscopy with shaped femtosecond pulses"; Opt. Express 11; 2003; pp. 1695-1701.
Drexler W. et al.; "In vivo ultrahigh-resolution optical coherence tomography"; Optics Letters; vol. 24, No. 17; Sep. 1, 1999; pp. 1221-1223.
Hasan, T. et al.; "Photodynamic Therapy of Cancer"; Chapter 40 in Holland Frei Cancer Medicine; BC Dekker Inc.; 2003; (55 pages).
Sharman, W.M. et al.: "Targeted photodynamic therapy via receptor mediated delivery systems"; Adv. Drug Delivery Rev. 56(1); Jan. 2004; pp. 53-76.
Assion, A. et al; "Control of Chemical Reactions by Feedback-Optimized Phase-Shaped Femtosecond Laser Pulses"; Science Magazine, vol. 282; Oct. 30, 1998; pp. 919-922.
Warren, W.S.; "Chemistry with photons"; Science, vol. 262; Nov. 12, 1993; pp. 1008-1009.
Chilla, Juan L.A. et al.; "Direct determination of the amplitude and the phase of femtosecond light pulses"; Optics Letters; vol. 16, No. 1; Jan. 1, 1991; pp. 39-41.
Kim, D.S. et al; "Femtosecond pulse distortion in GaAs quantum wells and its effect on pump-probe or four-wave-mixing experiments"; Physical Review B; vol. 50, No. 24; Dec. 15, 1994; pp. 18240-18249.
Kaindl, Robert A. et al.; "Generation, shaping, and characterization of intense femtosecond pulses tunable from 3 to 20 μm"; J. Opt. Soc. Am. B; vol. 17, No. 12; Dec. 2000; pp. 2085-2094.
Panasenko, Dmitriy et al.; "Single-shot sonogram generation for femtosecond laser pulse diagnostics by use of two-photon absorbtion in a silicon CCD camera"; Optics Letters; vol. 27, No. 16; Aug. 15, 2002; pp. 1475-1477.
Baltuska, Andrius et al.; "Visible pulse compression to 4 fs by optical parametric amplification and programmable dispersion control"; Optics Letters; vol. 27, No. 5; Mar. 1, 2002; pp. 306-308.
Meshulach D. et al.; "Adaptive ultrashort pulse compression and shaping"; Optics Communications 138; 1997; pp. 345-348.
Brixner, T. et al.; "Feedback-controlled femtosecond pulse shaping"; Appl. Phys. B 70 (Suppl); 2000; pp. S119-S124.
Stobrawa, G. et al.; "A new high-resolution femtosecond pulse shaper"; Appl. Phys. B 72; 2001; pp. 627-630.
Hacker, M. et al.; "Frequency doubling of phase-modulated, ultrashort laser pulses"; Appl. Phys. B 73; 2001; pp. 273-277.
Weiner, Andrew M. et al.; "Femtosecond Pulse Shaping for Synthesis, Processing and Time-to-Space Conversion of Ultrafast Optical Waveforms"; IEEE Journal of Selected Topics in Quantum Electronics; vol. 4, No. 2; Mar./Apr. 1998; pp. 317-331.
Dudovich, N et al; "Transform-limited pulses are not optimal for resonant multiphoton transitions"; Phys. Rev. Lett. 86; 2001; pp. 47-50.
Hillegas, C.W. et al.; "Femtosecond laser pulse shaping by use of microsecond radiofrequency pulses"; Optics Letters; vol. 19, No. 10; May 15, 1994; pp. 737-739.
Weiner, A.M. et al.; "Programmable Shaping of Femtosecond Optical Pulses by Use of 128-Element Liquid Crystal Phase Modulator"; IEEE Journal of Quantum Electronics; vol. 28, No. 4; Apr. 1992; pp. 908-920.
Matuschek. N.; "Back-side-coated chirped mirrors with ultrasmooth broadband dispersion characteristics"; Applied Physics B 71; Sep. 6, 2000; pp. 509-522.
Ding. Y.; "Femtosecond pulse shaping by dynamic holograms in photorefractive multiple quantum wells"; Optics Letters; vol. 22, No. 10; May 15, 1997; pp. 718-720.

Imeshev, G. et al. "Engineerable femtosecond pulse shaping by second-harmonic generation with Fourier synthetic quasi-phase-matching gratings"; Optics Letters; vol. 23, No. 11; Jun. 1, 1998; pp. 864-866.
Tull, J.X. et al.; "High-Resolution, Ultrafast Laser Pulse Shaping and Its Applications"; Advances in Magnetic and Optical Resonance; vol. 20; 1997; pp. 1-65.
Weiner, A.M.; "Femtosecond pulse shaping using spatial light modulators"; Rev. Sci. Instrum. vol. 71(5); 2000; pp. 1929-1960.
Schreier, F. et al.; "Femtosecond pulse shaping with a stratified diffractive structure"; Optics Communications 185; 2000; pp. 227-231.
Bhattacharya, N. et al.; "Implementation of Quantum Search Algorithm using Classical Fourier Optics"; Phys. Rev. Lett.; vol. 88. No. 13; Apr. 1, 2002; p. 137901-1-137901-4.
Baumert, T. et al. "Femtosecond pulse shaping by an evolutionary algorithm with feedback"; Appl. Phys. B 65; 1997; pp. 779-782.
Hornung, Thomas et al.; "Adapting optimum control theory and using learning loops to provide experimentally feasible shaping mask patterns"; Journal of Chemical Physics; vol. 115, No. 7; Aug. 15, 2001; pp. 3105-3111.
Meshulach, D. et al.; "Adaptive real-time femtosecond pulse shaping"; J. Opt. Soc. Am. B; vol. 15, No. 5; May 1998; pp. 1615-1619.
Zeidler, D. et al.; "Adaptive compression of tunable pulses from a non-colinear-type Opa to below 16 fs by feedback-controlled pulse shaping"; Appl. Phys. B 70 (Suppl); 2000; pp. S125-S131.
Brixner, T., A. Oehrlein, M. Strehle, and G. Gerber "Feedback-controlled femtosecond pulse shaping" Applied Physics B 70 [Suppl.], S119-S124 (2000).
O'Shea, Patrick, Mark Kimmel, Xun Gu, and Rick Trebino "Highly simplified device for ultrashort-pulse measurement" Optics Letter/ vol. 26, No. 12 / Jun. 15, 2001.
Zheng, Z. and A.M. Wolfe "Coherent control of second harmonic generation using spectrally phase coded femtosecond waveforms" Chemical Physics 267 (2001) 161-171 (Received Aug. 31, 2000).
Foing, J.P. et al. "Femtosecond Pulse Phase Measurement by Spectrally Resolved Up-Conversion—Application to Continuum Compression," IEEE J. Quantum Electron. 28, 2285 (1992).
Rhee, T.K. et al. "Chirped-Pulse Amplification of 85-Fs Pulses at 250 Khz with 3rd-Order Dispersion Compensation by Use of Holographic Transmission Gratings," Opt. Lett. 19, 1550 (1994).
Albrecht, T.F. et al. "Chirp Measurement of Large-Bandwidth Femtosecond Optical Pulses Using 2-Photon Absorption," Opt. Commun. 84, 223 (1991).
Ranka et al., "Autocorrelation Measurement of 6-fs Pulses Based on the Two-Photon-induced Photocurrent in a GaAsP Photodiode," Opt. Lett. 22 (17), 1344-1346 (1977).
Rivet, S. et al., "Complete pulse characterization: measurements of linear and nonlinear properties" Opt. Commun. 181, 425-435 (2000).
Weiner, A.M. "Ultrafast Optics" Chapter 3 entitled "Ultrafast-Pulse Measurement Methods" (pp. 85-146), (2009).
Dantus, Marcos et al. "Two-photon microscopy with Sub-8fs laswer pulse" PDPA Frontiers in Optics/Laser Science XXVI; Oct. 24-28, 2010, pp. 1-18.
Eramo, R. et al. "Third-harmonic generation in positively dispersive gases with a novel cell", vol. 33, No. 9, Applied Optics, 20 Mar. 1994, pp. 1691-1696.
Kroner D et al: "Asymmetric laser excitation in chiral molecules: quantum simulations for a proposed experiment", Chemical Physics Letters Elsevier Netherlands, vol. 372, No. 1-2, Apr. 22, 2003, pp. 242-248, XP002431288, ISSN: 0009-2614, figure 3.
Dela Cruz Johanna M et al: "Multidimensional Analysis With Shaped Femtosecond Pulses: Identification of Conformational and Geometric Isomers and Mixtures Using Mass Spectrometry," American Chemical Society. Abstracts of Paper. At the National Meeting, American Chemical Society, Washington, DC, US, vol. 230, Aug. 28, 2005, p. U418, XP009082815, ISSN: 0065-7727, the whole document.
Dela Cruz J M et al: "Quantitative mass spectrometric identification of isomers applying coherent laser control," Journal of Physical Chemistry A ACS USA, vol. 109, No. 38, Sep. 29,2005, pp. 8447-8450, XP002431289, ISSN: 1089-5639, figure 1.

(56) References Cited

OTHER PUBLICATIONS

Dantus Marcos et al: "Stereoisomer Recognition by Ms With Shaped Laser Pulses," American Chemical Society. Abstracts of Paper. At the National Meeting, American Chemical Society, Washington, DC, US, vol. 231, Mar. 26, 2006, pp. 1-Anyl, XP009082814, ISSN: 0065-7727, the whole document.
Hoki K et al: "Locally Designed Pulse Shaping for Selective Preparation of Enantiomers From Their Racemate" Journal of Chemical Physics, New York, Ny, US, vol. 114, No. 4, Jan. 22, 2001 (2001-01-22), pp. 1575-1581, XP009082805, ISSN: 0021-9606, p. 1580.
Bychkov S S et al: "Laser synthesis of chiral molecules in isotropic racemic media", Journal of Experimental and Theoretical Physics, Nauka/Interperiodica, MO, vol. 93, No. 1, Jul. 1, 2001, pp. 24-32, XP019306789, ISSN: 1090-6509, p. 26-p. 27.
Hoki K et al: "Selective preparation of enantiomers from a racemate by laser pulses: model simulation for oriented atropisomers with coupled rotations and torsions," Chemical Physics Elsevier Netherlands, vol. 267, No. 1-3, Jun. 1, 2001, pp. 59-79, XP002431290, ISSN: 0301-0104, p. 76-p. 77.
Brixner T et al: "Quantum control by ultrafast polarizaton shaping," Phys Rev Lett; Physical Review Letters May 21, 2004, vol. 92, No. 20, May 21, 2004, pp. 208301-208301, XP002442133, figures 2,4.
Thanopulos I et al: "Laser-driven coherent manipulation of molecular chirality," Chemical Physics Letters Elsevier Netherlands, vol. 390, No. 1-3, May 21, 2004, pp. 228-235, XP002442134, ISSN: 0009-2614, pp. 232-234.
Atabek O et al: "Intense laser control of the chemical bond," Theochem Elsevier Netherlands, vol. 493, Dec. 15, 1999, (1999-12-15), pp. 89-101, XP002442135, ISSN: 0166-1280, pp. 96-99.
Lozovoy V et al: "Multiphoton intrapulse interference. IV. Ultrashort laser pulse spectral phase characterization and compensation," Optics Letters, OSA, Optical Society of America, Washington, DC, US, vol. 29, No. 7, Apr. 1, 2004, pp. 775-777, XP002434949, ISSN: 0146-9592, pp. 775-776.
Pelfang Tian et al: Femtosecond phase-coherent two-dimensional spectroscopy, Science American Assoc. Adv. Sci USA, vol. 300, No. 5625, Jun. 6, 2003, pp. 1553-1555, XP002442136 ISSN: 0036-8075, p. 1553.
Motzkus M: "Open and closed loop control of complex molecules with shaped fs pulses," 2003 International Conference Physics and Control. Proceedings (Cat. No. 03EX708) IEEE Piscataway, NJ, USA, vol. 3, 2003, p. 746 vol. 3, XP010660595, ISBN: 0/7803-7939-X, columns 1-2.
Ma R et al: "Intense femtosecond laser field-induced Coulomb fragmentation of C21-14," International Journal of Mass Spectrometry, Elsevier, Amsterdam, NL, vol. 242, No. 1, Mar. 15, 2005, pp. 43-48, XP004764925, ISSN: 1387-3806, p. 47.
Wu C et al: "Mass and photoelectron spectrometer for studying field-induced ionization of molecules," International Journal of Mass Spectrometry, Elsevier Science Publishers, Amsterdam, NL, vol. 216, No. 3, May 15, 2002, pp. 249-255, XP004361125, ISSN: 1387-3806, pp. 251-252.
Chen J et al: "Femtosecond laser-induced dissociative ionization and Coulomb explosion of ethanol," International Journal of Mass Spectrometry, Elsevier, Amsterdam, NL, vol. 241, No. 1, Feb. 15, 2005, pp. 25-29, XP004991894, ISSN: 1387-3806, p. 26.
Wu Chengyin et al: "Laser-induced dissociation and explosion of methane and methanol," J Phys B At Mol Opt Phys; Journal of Physics B: Atomic, Molecular and Optical Physics Jun. 14, 2002, vol. 35, No. 11, Jun. 14, 2002, pp. 2575-2582, XP002442137, pp. 2579-2582, col. 0.
Tomizawa H et al: "Development of automatically optimizing system of both spatial and temporal beam shaping for Uv-laser pulse," Proceedings of the SPIE—The International Society for Optical Engineering SPIE-Int. Soc. Opt. Eng USA, vol. 5481, No. 1, 2004, pp. 47-55, XP002442138, ISSN: 0277-786X, figures 2-4.
Yu Huang et al: "Application of adaptive feedback loop for ultraviolet femtosecond pulse shaper control," Optics Express Opt. Soc. America Usa, vol. 14, No. 21, Oct. 2006, XP002442139, ISSN: 1094-4087, figure 1.
Roth M et al: "Acousto-optic femtosecond pulse shaping in the ultraviolet," Lasers and Electro-Optics, 2005, (CLEO). Conference on Baltimore, MD, USA May 22-27, 2005, Piscataway, NJ, USA, IEEE, May 22, 2005, pp. 2244-2246, XP010877118, ISBN: 1-55752-795-4, figure 1.
Roth M et al: Acousto-optical shaping of ultraviolet femtosecond pulses, Applied Physics B; Lasers and Optics, Springer-Verlag, BE, vol. 80, No. 4-5, Apr. 1, 2005. pp. 441-444, XP019337359, ISSN: 1432-0649, figure 1.
Fowles, "Introduction to Modern Optics," 1989, Dover 2e, pp. 2-19.
Ogawa et al, Dependence of the Laser Two-Photon Ionization Process in Solution on the Laser Pulse Width, Analytical Chemistry, vol. 73, Mar. 20, 2001, pp. 2066-2069.
P. Main et al.; "Generation of Ultrahigh Peak Power Pulses by Chirped Pulse Amplification;" IEEE Journal of Quantum Electronics, vol. 24, No. 2, Feb. 1988; pp. 398-403.
P. K. Mukhopadhyay et al.; "All-Fiber Low-Noise High-Power Femtosecond Yb-Fiber Amplifier System Seeded by an All-Normal Dispersion Fiber Oscillator;" IEEE Journal of Selected Topics in Quantum Electronics, vol. 15, No. 1, Jan./Feb. 2009; pp. 145-152.
Limped J. et al.; "All fiber chirped-pulse amplification system based on compression in air-guiding photonic bandgap fiber;" Optics Express, vol. 11, No. 24, Dec. 1, 2003; pp. 3332-3337.
Strickland D. et al.; "Compression of amplified chirped optical pulses;" Optics Communications, vol. 56, No. 3; Dec. 1, 1985; pp. 219-221.
Chirped pulse amplification; Internet excerpt from Wikipedia; published on Aug. 7, 2008; 4 pages.
Backus S. et al.; "High power ultrafast lasers;" Review of Scientific Instruments, vol. 69, No. 3, Mar. 1998; pp. 1207-1223.
Xu L. et al.; "Experimental generation of an ultra-broad spectrum based on induced-phase modulation in a single-mode glass fiber;" Optics Communications, 162 (1999); pp. 256-260.
Weiner A.M.; "Femtosecond pulse processing;" Optical and Quantum Electronics 32, 2000; pp. 473-487.
Efimov A. et al.; "Programmable dispersion compensation and pulse shaping in a 26-fs chirped-pulse amplifier;" Optics Letters, vol. 23, No. 20, Oct. 15, 1998; pp. 1612-1614.
"Shape Your Pulses. Control Your Experiment." advertisement, Laser Focus World, (Dec. 1997) p. 26, CRI, Inc.
Barry, Liam P., et al., "A High-Speed Optical Star Network Using TDMA and All-Optical Demultiplexing Techniques", IEEE Journal on Selected Areas in Communications, vol. 14, No. 5, (Jun. 1996), pp. 1030-1038.
Beadie, G. et al.; "Towards a Fast-Cars anthrax detector: CARS generation in a DPA surrogate molecule"; Journal of Modem Optics, vol. 50, No. 15-17, 2003, pp. 2361-2368.
Bender, Daniel A., et al., "Modified spectrum autointerferometric correlation (Mosaic) for single-shot pulse characterization," Optics Letters, vol. 32, No. 19 (Oct. 1, 2007) Optical Society of America, pp. 2822-2824.
Butcher, Steve, et al., "Multiphoton approach shapes ultrafast pulses," Pulse Shaping, (2006) Institute of Physics and IOP Publishing Ltd., 3 pages.
Butenko, A.V. et al.; "Factals: Giant Impurity Nonlinearities in Optics of Fractal Clusters;" Z. Phys. D., 10, 1988; pp. 81-92.
CheckGate 9000—Metal detector; Internet publication from Safer America (2003) http://www.saferamerica.com/productDetail. asp?categoryID=19&productID=234; printed Oct. 6, 2004 (3 pages).
Dantus, Marcos, et al., "Miips characterizes and corrects femtosecond pulses," Ultrafast Optical Systems, Laser Focus World, (May 2007) XP001539450, 4 pages.
Dela Cruz, J. M. et al.; "Coherent Control Improves Biomedical Imaging With Ultrashort Shaped Pulses;" Journal of Photochemistry and Photobiology A: Chemistry 180, Mar. 2006; pp. 307-313.
Delfyett, Peter J., et al., "High-Power Ultrafast Laser Diodes", IEEE Journal of Quantum Electronics, vol. 28, No. 10, (Oct. 1992), pp. 2203-2219.
Delong, K.W., et al., "Frequency Resolved Optical Gating with the Use of 2nd-Harmonic Generation." Journal of Optical Society of America B—Optical Physics, 1994. 11 (11): pp. 2206-2215.

(56) References Cited

OTHER PUBLICATIONS

Dreischuh, a., Experimental Demonstraction of Pulse Shaping and Shortening by Spatial Filtering of an Induced-Phase-Modulated Probe Wave, IEEE Journal of Quantum Electronics, vol. 33, No. 3, (Mar. 1997), pp. 329-335.
Dugan, M.A., et al., "High-resolution acousto-optic shaping of unamplified and amplified femtosecond laser pulses", J. Opt. Soc. Am. B, vol. 14, No. 9, (Sep. 1997), pp. 2348-2358, Optical Society of America.
Efimov, a., et al., "Programmable shaping of ultrabroad-bandwidth pulses from a Ti:sapphire laser", Journal B/vol. 12, No. 10 (Oct. 1995) pp. 1968-1980, Optical Society of America.
EVD-3000®—Hand-held Explosives Detector, Internet Publication, http://www.saferamerica.com/productDetail.asp?categoryID=16 &productID=235; printed Oct. 6, 2004 (3 pages).
Fermann, M.E., et al., "Additive-pulse-compression mode locking of a neodymium fiber laser", Optics Letters, vol. 16, No. 4, (Feb. 15, 1991), Optical Society of America.
Fetterman, et al., "Ultrafast pulse shaping: amplification and characterization", Optics Express, vol. 3, No. 10, (Nov. 9, 1998), pp. 366-375.
Fork, R.L., et al., "Compression of optical pulses to six femtoseconds by using cubic phase compensation", Optics Letters, (Jul. 1987), vol. 12, No. 7, Optical Society of America.
Fujimoto, Masatoshi, et al., "Programmable shaping of a subterawatt, femtosecond laser pulse by modulating the spectral phase of the preamplified pulse," Optics Communications, 280 (2007) ScienceDirect, pp. 404-407.
Galler, A., et al., "Pulse shaper assisted short laser pulse characterization," Applied Physics B90, Lasers and Optics (Jan. 2008) pp. 427-430.
Gallmann, L., et al., "Characterization of sub-6-fs optical pulses with spectral phase interferometry for direct electric-field reconstruction," Optics Letters, vol. 24, No. 18 (Sep. 15, 1999) p. 13140-1316.
Gomes, A.S.L., et al., "Optical fibre-grating pulse compressors", Tutorial Review, Optical and Quantum Electronics 20, (1988), pp. 95-112.
Gunaratne, T. et al.; "Influence of Bandwidth and Phase Shaping on Laser Induced Breakdown Spectroscopy With Ultrashort Laser Pulses;" Chemical Physics Letters 423, Apr. 3, 2006; pp. 197-201.
Gunn, J M et al: "Polarization and phase control of remote surface-plasmon-mediated twophoto-induced emission and waveguiding" Nano Letters American Chem. Soc. USA, vol. 6, No. 12, Aug. 2006.
Haner, M., et al., "Generation of programmable, picosecond-resolution shaped laser pulses by fiber-grating pulse compression", Optics Letters, vol. 12, No. 6, (Jun. 1987), pp. 398-400, Optical Society of America.
Hanna, Sherif F. et al.; "Electronic-resonance-enhanced coherent anti-Stokes Raman spectroscopy of nitric oxide"; Applied Physics Letters; vol. 83, No. 9, Sep. 1, 2003; pp. 1887-1889.
Heritage, J.P., "Picosecond pulse shaping by spectral phase and amplitude manipulation", Optics Letters, vol. 10, No. 12, (Dec. 1985), pp. 609-611, Optical Society of America.
Kapteyn, Henry C. et al.; "A Comparison of Multipass Vs. Regenerative Ti:Sapphire Laser Amplifiers;" Kapteyn-Murnane Laboratories Inc., Boulder, COo, USA, www.kmlabs.com; (2003) 2 pages.
Kolenda, Jürgen, et al., "Pulse Shaping with the MIIPS-Process," Laser Technology, (Jan. 2008) Photonik International, p. 68.
Konorov, S.O., "Laser Breakdown with Millijoule Trains of Picosecond Pulses Transmitted through a Hollow-Core Photonic-Crystal Fiber", Laser Physics, vol. 13, No. 4, (2003) pp. 652-656.
Kosik, Ellen M., et al., "The effects of noise on ultrashort optical pulse measurement using Spider"; The Institute of Optics, University of Rochester, Rochester, NY; (2000) pp. 21-23.
Krausz, F., et al., "Generation of 33-fs optical pulses from a solid-state laser", Optics Letters, (Feb. 1, 1992), vol. 17, No. 3, Optical Society of America.
Lee, P.C. et al.; "Adsorption and Surface-Enhanced Raman of Dyes on Silver and Gold Sols;" Phys. Chem., vol. 86, No. 17, 1982, pp. 3391-3395.
Lemoff, B.E., et al., "Quintic-phase-limited, spatially uniform expansion and recompression of ultrashort optical pulses", Optics Letters, vol. 18, No. 19, (Oct. 1, 1993), pp. 1651-1653, Optical Society of America.
Link, Stephan et al.; "Optical Properties and Ultrafast Dynamics of Metallic Nanocrystals;" Annu. Rev. Phys. Chem. 54, 2003; pp. 331-369.
Liu, Yongqian, et al., "Terahertz Waveform Synthesis via Optical Pulse Shaping", IEEE Journal of Selected Topics in Quantum Electronics, (Septmeber 1996), vol. 2, No. 3, pp. 709-719.
Lozovoy, V. V. et al.; "Spectral Phase Optimization of Femtosecond Laser Pulses for Narrow-Band, Low-Background Nonlinear Spectroscopy;" Optics Express, vol. 13, No. 26, Dec. 26, 2005; pp. 10882-10887.
Meshulach, D., et al., "Adaptive Compression of Femtosecond Pulses", presented at the Ultrafast Optics 1997 Conference, Aug. 1997, Monterey California (3 pages).
Midorikawa, Katsumi, et al., "Phase-Matched High-Order Harmonic Generation by Guided Intense Femtosecond Pulses," IEEE Journal of Selected Topics in Quantum Electronics, vol. 5, No. 6 (Nov./Dec. 1999) pp. 1475-1485.
N.H. Damrauer et al.; "Control of bond-selective photochemistry in CH2BrCI using adaptive femtosecond pulse shaping"; The European Physical Journal D, 20, 2002; pp. 71-76.
Nisoli, M., et al., "Compression of high-energy laser pulses below 5fs", Optics Letters, (Apr. 15, 1997) vol. 22, No. 8, pp. 522-524, Optical Society of America.
Ogilvie, Jennifer P., et al., "Use of coherent control for selective two-photon fluorescence microscopy in live organisms," Optical Society of America (Jan. 2006) 8 pages.
Ohno, Kimihisa, et al., "Adaptive pulse shaping of phase and amplitude of an amplified femtosecond pulse laser by direct reference to frequency-resolved optical gating traces," J. Opt. Soc. Am. B vol. 19, No. 11 (Nov. 2002) pp. 2781-2790.
Parmeter, John E., et al., "Overview of Explosives Detection Research and Development in Department 5848 at Sandia National Laboratories"; 16th Annual NDA Security Technology Symposium & Exhibition; Jun. 26-29, 2000.
Pastirk, I. et al.; "Femtosecond Ground State Dynamics of Gas Phase N2O4 and NO2," Chemical Physics letters, vol. 349, Nov. 23, 2001; pp. 71-78.
Pastirk, I., et al., "No loss spectral phase correction and arbitrary phase shaping of regeneratively amplified femtosecond pulses using MIIPS," Optics Express, vol. 14, No. 20, (Oct. 2, 2006) pp. 9537-9543.
Paul R. Bolton et al.; "Propagation of intense, ultrashort laser pulses through metal vapor: refraction-limited behavior for single pulses"; J. Opt. Soc. Am. B, vol. 13, No. 2; Feb. 1996; pp. 336-346.
Perry, Michael D., et al., "Terawatt to Petawatt Subpicosecond Lasers", Articles, (May 13, 1994), vol. 264, Science.
Posthumus, J.H., "The dynamics of small molecules in intense laser fields," Reports on Progress in Physics, 67 (2004) Institute of Physics Publishing, pp. 623-665.
Quiroga-Teixeiro, M.L., et al., "Compression of optical solitons by conversion of nonlinear modes", J. Opt. Soc. Am. B, vol. 12, No. 6, (Jun. 1995), pp. 1110-1116, Optical Society of America.
R. Wolleschensky et al.; "Characterization and Optimization of a Laser-Scanning Microscope in the Femtosecond Regime;" Applied Physics B 67, Lasers and Optics, 1998; pp. 87-94.
Reitze, D.H., et al., "Shaping of wide bandwidth 20 femtosecond optical pulses", Appl. Phys. Lett. 61 (11), (Sep. 14, 1992), pp. 1260-1262, American Institute of Physics.
Rodriguez, George, et al., "Coherent Ultrafast MI-FROG Spectroscopy of Optical Field Ionization in Molecular H2, N2, and O2," IEEE Journal on Selected Topics in Quantum Electronics, vol. 7, No. 4 (Jul./Aug. 2001) pp. 579-591.
Sanders, a. W. et al.: "Observation of Plasmon Propagation, Redirection, and Fan-Out in Silver Nanowires" Nano Letters, American Chemical Society, Washington, DC, US, vol. 6, No. 8, Jun. 28, 2006, pp. 1822-1826, XP007901978, ISSN: 1530-6984.
Sandia tests new Faa explosives—detection portal at Albuquerque International Airport; Internet publication from Safer America, Sep. 15, 1997.

(56) References Cited

OTHER PUBLICATIONS

ScanMail 10K—Scanna; Internet publication from Safer America; 2003.

Serbin, J., et al., "Femtosecond lasers as novel tool in dental surgery," applied surface science, 197-198 (2002) pp. 737-740.

Sergey Yeremenko et al.; "Frequency-resolved pump-probe characterization of femtosecond infrared pulses"; Optics Letters, vol. 27, No. 13; Jul. 1, 2002; pp. 1171-1173.

Shimizu, Satoru, et al., "Spectral phase transfer for indirect phase control of sub-20-fs deep UV pulses," Optics Express, vol. 13, No. 17 (Aug. 22, 2005) pp. 6345-6353.

Siders, C.W., et al., "Blue-shifted third-harmonic generation and correlated self-guiding during ultrafast barrier suppression ionization of subatmospheric density noble gases," J. Opt. Soc. Am. B/vol. 13, No. 2 (Feb. 1996) pp. 330-335.

Spielmann, C., et al., "Ti: Sapphire Laser Produces Intense Sub-5-FS Pulses", Laser Focus World, May 97, vol. 33, Issue 5, p. 127.

Stockman, Mark I. et al.; "Coherent Control of Femtosecond Energy Localization in Nanosystems;" Physical Review Letters, vol. 88, No. 6, Feb. 11, 2002; pp. 067402-1-067402-4.

Surharev, Maxim et al.; "Coherent Control Approaches to Light Guidance in the Nanoscale;" The Journal of Chemical Physics 124, 2006; XP008086379; pp. 144707-1-144707-8.

Szipöcs, Robert, et al., "Chirped multilayer coatings for broadband dispersion control in femtosecond lasers", Optics Letters, (Feb. 1, 1994), vol. 19, No. 3, Optical Society of America.

Tamaki, Y., "Phase-matched third-harmonic generation by nonlinear phase shift in a hollow fiber," Lasers and Optics Applied Physics B, vol. 67, (1998) pp. 59-63.

Trebino, Rick, et al., "Using phase retrieval to measure the intensity and phase of ultrashort pulses: frequency-resolved optical gating", J. Opt. Soc. Am. A, vol. 10, No. 5, (May 1993), pp. 1101-1111, Optical Society of America.

Umstadter, D., et al., "Nonlinear Plasma Waves Resonantly Driven by Optimized Laser Pulse Trains", Physical Review Letters, vol. 72, No. 8, (Feb. 21, 1994), pp. 1224-1227, The American Physical Society.

Verluise, Frederic, et al., "Arbitrary dispersion control of ultrashort optical pulses with acoustic waves," J. Opt. Soc. Am. B vol. 17, No. 1 (Jan. 2000) pp. 138-145.

von Vacano, Bernhard, et al., "Shaper-assisted collinear SPIDER: fast and simple broadband pulse compression in nonlinear microscopy," vol. 24, No. 5, (May 2007) J. Opt. Soc. Am. B, pp. 1091-1100.

Warren, W.S., et al., "Coherent Control of Quantum Dynamics: The Dream is Alive", Articles, Science, (Mar. 12, 1993), vol. 259.

Wefers, Marc M., "Programmable phase and amplitude femtosecond pulse shaping", Optics Letters (Dec. 1, 1993), vol. 18, No. 23, pp. 2032-2034.

Weiner, "Encoding and decoding of femtosecond pulses", Optics Letters, (Apr. 1988), vol. 13, No. 4, Optical Society of America.

Weiner, A.M., "Enhancement of coherent charge oscillations in coupled quantum wells by femtosecond pulse shaping", J. Opt. Soc. Am. B, vol. 11, No. 12, (Dec. 1994), pp. 2480-2491, Optical Society of America.

Weiner, A.M., "Femtosecond Optical Pulse Shaping and Processing", Prog. Quant. Electr. (1995) vol. 19, pp. 161; 230-233.

Weiner, A.M., "High-resolution femtosecond pulse shaping", J. Opt. Soc. Am. B., vol. 5, No. 8, (Aug. 1988), pp. 1563-1572, Optical Society of America.

Weiner, A.M., "Programmable femtosecond pulse shaping by use of a multielement liquid-crystal phase modulator", Optics Letters, (Mar. 15, 1990), vol. 15, No. 6, pp. 326-328, Optical Society of America.

Weiner, A.M., "Spectral holography of shaped femtosecond pulses", Optics Letters, vol. 17, No. 3 (Feb. 1, 1992), pp. 224-226, Optical Society of America.

Weiner, A.M., et al., "Femtosecond multiple-pulse impulsive stimulated Raman scattering spectroscopy", J. Opt. Soc. Am. B., vol. 8, No. 6, (Jun. 1991), pp. 1264-1275.

Weiner, Andrew M., Programmable Shaping of Femtosecond Optical Pulses by Use of 128-Element Liquid Crystal Phase Modulator, (1992) vol. 28, No. 4, pp. 908-919, IEEE Journal of Quantum Electronics.

Wu, C. et al., Mass and Photoelectron Spectrometer for Studying Field-Induced Ionization of Molecules, International Journal of Mass Spectrometry, Elsevier Science Publishers, Amsterdam, NL, vol. 216, No. 3, May 15, 2002, pp. 249-255.

Xu, B et al.; "Quantitative Investigation of the Multiphoton Intrapuse Interference Phase Scan Method for Simultaneous Phase Measurement and Compensation of Femtosecond Laser Pulses;" J. Opt. Soc. Am. B, vol. 23, No. 4, Apr. 2006; pp. 750-759.

Xu, J.H., et al., "Study of Pulse Compression from 1.5 μm Distributed Feedback Lasers by a Gires-Tournois Interferometer", Fiber and Integrated Optics, vol. 13, (1994), pp. 365-372.

Yaron Silberberg; "Physics at the attosecond frontier"; Nature, vol. 414, Nov. 29, 2001; pp. 494-495.

Zhou, Jianping, et al., "Generation of 21-fs millijoule-energy pulses by use of Ti:sapphire", Optics Letters, vol. 19, No. 2, (Jan. 15, 1994), pp. 126-128, Optical Society of America.

\* cited by examiner

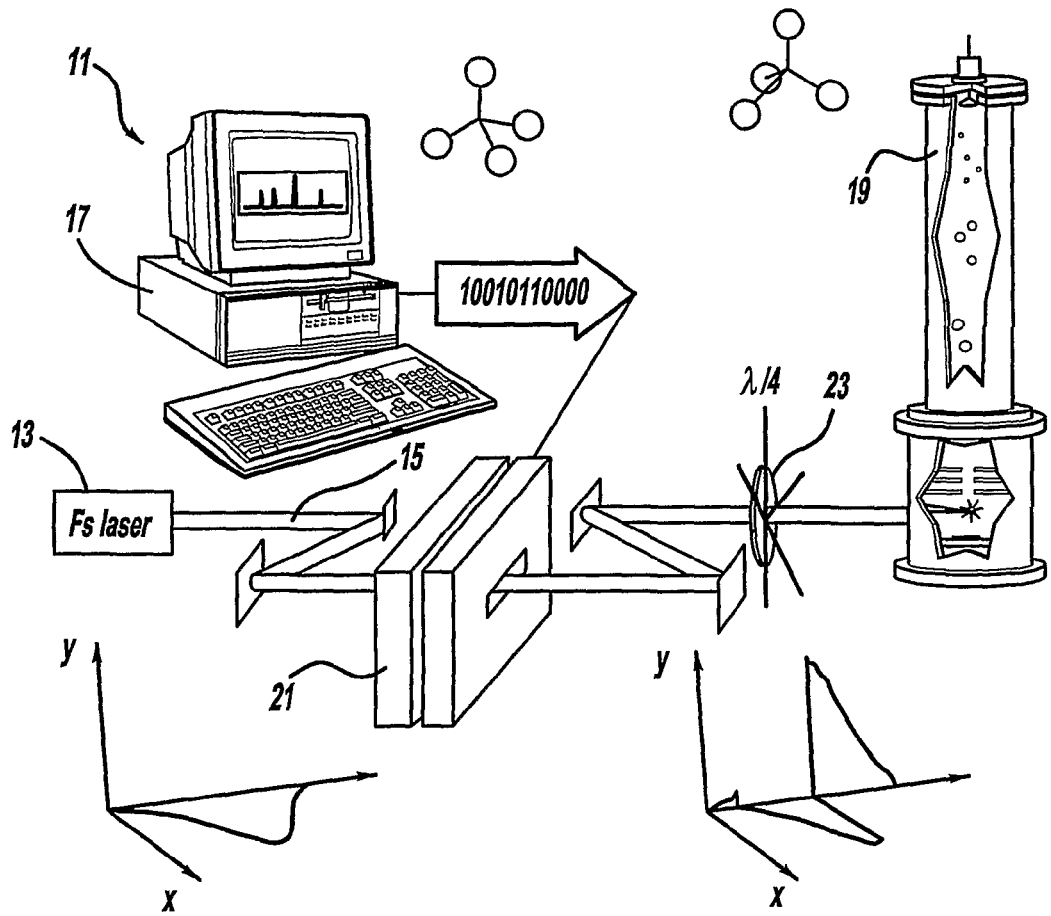
FIG-1
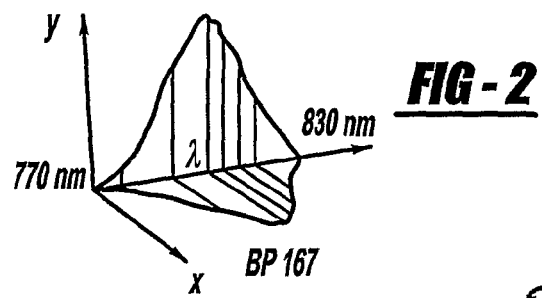
FIG-2
FIG-3a  FIG-3b

LASER BASED IDENTIFICATION OF MOLECULAR CHARACTERISTICS

CROSS-REFERENCE TO RELATED APPLICATIONS

This application is a 371 U.S. National Stage of International Application No. PCT/US2006/045686, filed Nov. 29, 2006 and published in English as WO 2007/064703 A2 on Jun. 7, 2007, which claims the benefit of U.S. Provisional Application No. 60/740,898, filed Nov. 30, 2005. The disclosures of the above applications are expressly incorporated herein by reference.

STATEMENT OF GOVERNMENT INTEREST

This invention was made with government support under CHE0500661 awarded by the National Science Foundation. The government has certain rights in the invention.

BACKGROUND OF THE INVENTION

This invention generally relates to laser pulse shaping and more specifically to identifying molecular characteristics with a shaped laser pulse.

The almost exclusive handedness of the essential building blocks of life, illustrated by left-handed amino acids and right-handed carbohydrates, is one of the most intriguing scientific questions. Interest in the analysis of optically active compounds has grown considerably because of their importance in the biochemical and pharmaceutical industries. In a number of cases, one optically active form of a drug is effective while the other is inactive and can have undesirable side effects. The large-scale resolution of chiral compounds is presently carried out by crystallization, by chemical reaction with chiral reagents, by chromatography (particularly, simulated moving bed (SMB) techniques) or by newer technologies (for example, membranes/automated screening or counter current extractions). Drug discovery and metabolic analysis, however, involve very small quantities of optically active compounds and could benefit from much greater sensitivity. Similarly, the search for the origin of chiral purity found in living organisms requires the ability to identify extremely small quantities of chiral compounds that may be present in meteorites. Increased chiral sensitivity has already shown that right-handed amino acids are present in a number of organisms as post translational modifications.

Some studies have been conducted using polarization pulse shaping and an evolutionary learning algorithm selecting a limited number of tests from a very large quantity of shaping variable possibilities. One such experiment is discussed in T. Brixner, et al., "Quantum Control by Ultrafast Polarization Shaping," Phys. Rev. Lett. 92, 20-8301 (2004).

SUMMARY OF THE INVENTION

In accordance with the present invention, enantiomers are characterized, identified, synthesized and/or modified by a shaped laser pulse. In another aspect of the present invention, binary shaping and circular polarization are employed with a laser pulse. A further aspect of the present invention provides a quarter-wave plate to convert horizontal and vertically polarized light into right or left circularly polarized light which allows for testing pure linear polarization by rotating the plate. In yet another aspect of the present invention, a laser system uses a first pulse shaper to introduce multiphoton intrapulse interference phase scan (hereinafter "MIIPS") and linear chirp (if needed), a second pulse shaper to introduce binary and linear (for example, along the horizontal and vertical axes) polarization, and/or a quarter-wave plate to introduce circular polarization to the pulse. In yet another aspect of the present invention, a pulse shaper is used to introduce a combination of phase retardation and polarization rotation so as to prepare laser pulses having intense circularly polarized fields that rotate in the 10-100 fs timescale. Methods of using the present invention system are also provided.

Tailored laser pulses of the present invention are used for low concentration molecular identification, through chiral fields, which induce differential fragmentation of enantiomeric compounds. By coupling these intense laser pulses with a mass spectrometer, great (for example, single molecule) sensitivity and chiral resolution will be obtained. Enantiomeric pairs are non-superimposable mirror images of one another, often identified as right- or left-handed molecules with identical chemical properties, except when reacting with another chiral reagent such as enzymes. A mass spectrometer of the present invention uses chiral femtosecond laser pulses which act as photonic enzymes that preferentially fragment right or left handed molecules. Thus, the mass spectrometry of the present invention can now be used to identify all types of stereoisomers without additional chemical reactions, an important capability for a method with growing application to drug discovery and metabolic analysis. Conceptually, a chiral pulse causes asymmetric switching between right and left circularly polarized light, and leads to differential laser induced fragmentation and ionization in enantiomerically different molecules. A right-handed enantiomer will couple to the chiral electromagnetic field differently than a left handed enantiomer. Therefore, an intense pulse with a specific succession of right and left optical torques would thereby play the role of a chiral photonic enzyme, preferentially cleaving one of the enantiomers. Based on this physical model, the order of the applied set of torques should determine which of the enantiomer is preferentially cleaved. This is ideally suited for testing chirality in the manufacture of pharmaceuticals and protein sequencing, especially when the undesired chirality amino acids or molecules are in very low concentrations.

Furthermore, the present invention advantageously uses binary settings (0 and π, or right and left circular polarization, for example) instead of a continuum of overly large values to reduce the number of shaped pulses that need to be tested for effectiveness. This allows use of all possible shaped pulses but without the inaccuracies and delay of a genetic learning algorithm, with the preferred embodiment. Additional advantages and features of the present invention will become apparent from the following description taken in conjunction with the accompanying drawings.

BRIEF DESCRIPTION OF THE DRAWINGS

FIG. 1 shows a diagrammatic view of a preferred laser system of the present invention where a computer sends binary codes to a polarization shaper to flip the polarization of certain frequency regions of the pulse from x to y polarization. The shaped pulses then go through a quarter-wave plate and are focused on a mass spectrometer chamber where they cause preferential fragmentation of right- or left-handed molecules.

FIG. 2 is a graph showing a theoretical binary polarization pulse.

FIGS. 3a and 3b are graphs showing theoretical polarized propeller pulse shapes employed with the preferred embodi

DETAILED DESCRIPTION

Figure 4:
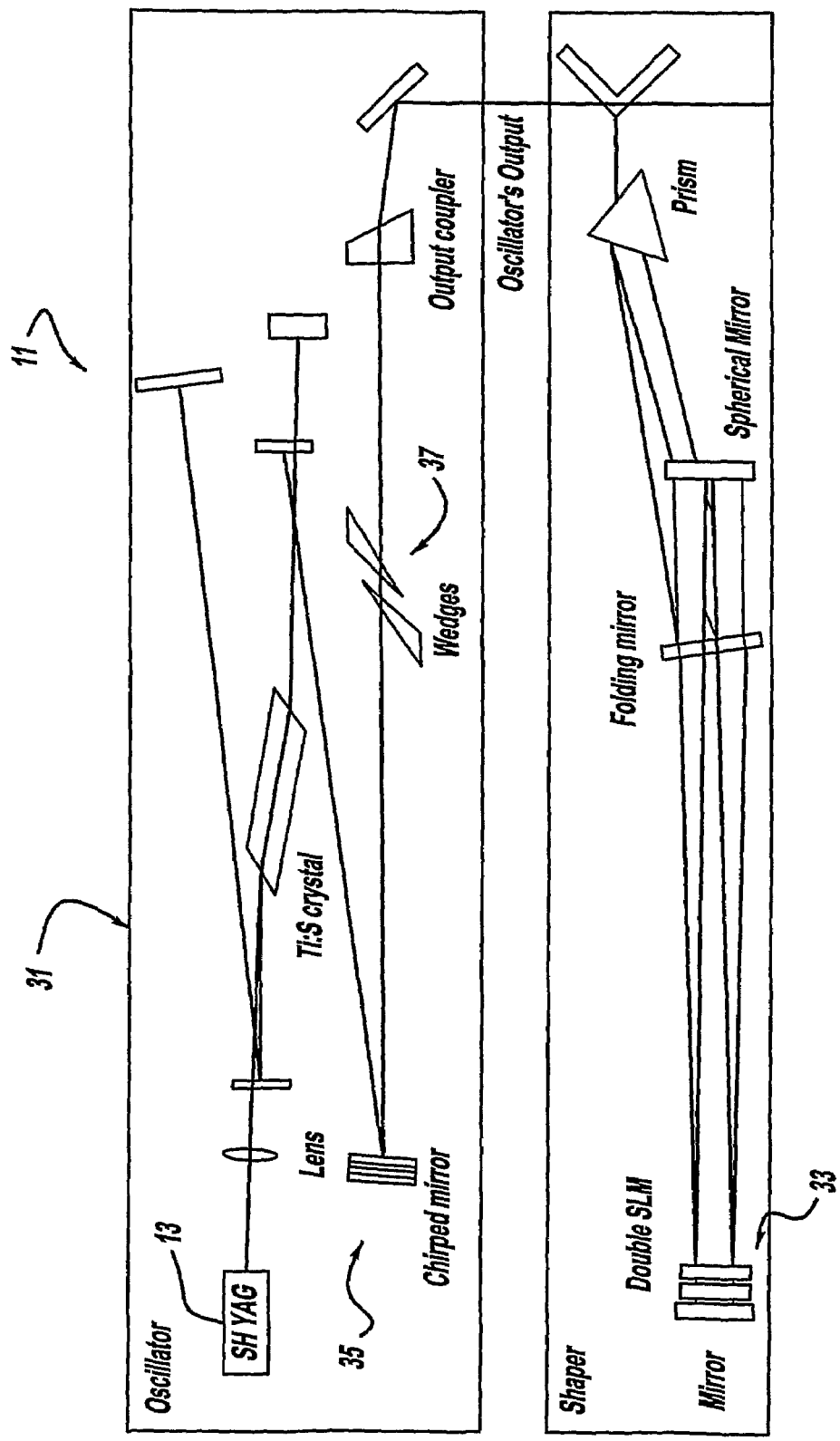
- FIG. 4 shows a first oscillator and shaper construction employed with the preferred embodiment laser system.

Referring to FIG. 1, a preferred embodiment of a laser system 11 of the present invention employs a femtosecond laser 13, operable of emitting laser beam pulses 15 of a duration of about 10-100 fs and preferably about 35 fs, a programmable computer controller 17 and a time-of-flight mass spectrometer 19. In the spectrometer, the electron impact source is replaced by amplified femtosecond laser pulses that are polarization shaped using a modified phase-amplitude pulse shaper 21. Pulse shaper 21 includes two gratings flanking a spatial light modulator which is at the Fourier plane. The laser pulse is dispersed in the frequency domain and discrete spectral regions are flipped from horizontal to vertical polarization. After spatial light modulator ("SLM") 21, a quarter-wave length plate 23 is optionally used to convert the linear polarization, vertical and horizontal, into circular polarization, right and left, respectively. This device allows the controller to quickly test pure linear polarization by rotating the quarter-wave plate (either manually or with an automatically controlled electromagnetic actuator). The binary polarized pulses are then focused on a small concentration of molecular species in the gas phase (approximately $10^4$ molecules interact with each laser pulse). The resulting ions and fragment ions are detected and identified by their time-of-flight to the detector. The combination of polarization shaping and the quarter-wave plate results in fields with rapidly switching circularly polarized light as shown in FIGS. 2, 3a and 3b.

The laser, pulse shaper, controller, mass spectrometer and a multiphoton intrapulse interference phase scan ("MIIPS") procedure are as disclosed in U.S. patent application Ser. No. 11/177,940, invented by Dantus et al. and filed on Jul. 8, 2005, which is incorporated by reference herein. Additionally, quarter-wave plate 23 is preferably a zero order, air spaced, CVI Laser, LLC Part No. QWPO-800-10-4-AS10 wave plate centered at the same wavelength as the fs laser pulse being used, preferably 800 nm. In the present example, a pulse shaper 21 is preferably a liquid crystal, dual mask, phase amplitude pulse shaper but other spatial light modulators based on acousto-optics or micro-electro-mechanical systems ("MEMS") may alternately be used.

Pulse shaping as used herein preferably controls the phase and amplitude of different frequency regions within the bandwidth of a femtosecond laser beam pulse. This manipulation is usually done in the frequency domain and results in large frequency and temporal changes in the output field. Polarization shaping as used herein preferably controls the direction in which the electric field is pointing for different frequencies within the bandwidth of the femtosecond pulse. Polarization is beneficial since molecules usually align their dipole moments in the direction of the electric field. Fast changes in the electric field direction causes torques in the molecules.

More specifically, femtosecond oscillators come in three main categories: very compact fiber based systems (~100-200 fs pulse duration), prism-compressed Ti:Sapphire systems (~10-20 fs), and chirped mirror compressed Ti:Sapphire systems (<10 fs). The latter can produce pulses with duration of about 5 fs and a spectrum stretching from 600 nm up to 1100 nm, a 100 MHz repetition rate and energy per pulse up to 1 nJ. A schematic illustration of one laser system 31 used is presented in FIG. 4, and it incorporates a prism based pulse shaper with a spatial light modulator at the Fourier plane 33. For super-short pulses, a grating is preferred instead of a prism. Chirped mirrors 35 and optical wedges 37 compensate intracavity spectral phase distortions and allow generation of an octave spanning laser spectrum. The ultra-broad bandwidth shaper compensates phase distortions remaining from the oscillator and pre-compensates those farther down the beam path.

Figure 5:
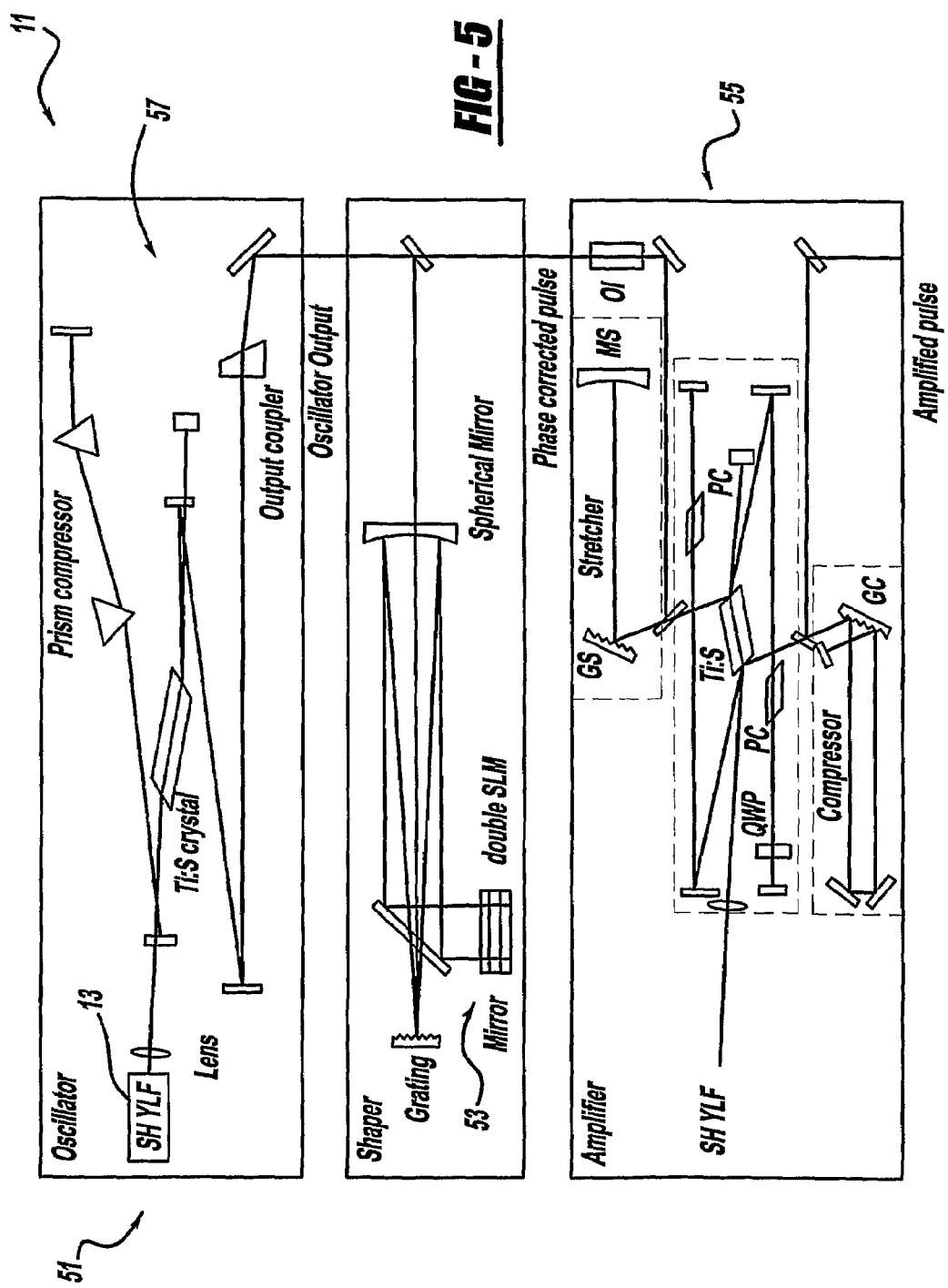
FIG. 5 shows a second oscillator, shaper and amplifier construction employed with the preferred embodiment laser system.

High energy laser systems can be divided broadly by their method of amplification into regenerative or multi-pass. Regenerative amplification provides a more efficient use of the gain and better stability; however, the regenerative amplification cavity results in greater phase distortions in the output pulse. Multi-pass amplification avoids some of these phase distortions by minimizing the number of optical elements and the number of times the laser pulse transmits through them. Shorter pulses can usually be achieved by multi-pass amplification but with greater alignment difficulty and lower pulse to pulse stability than the regenerative amplification systems. FIG. 5 shows a schematic of a high-energy laser system 51 capable of producing amplified phase shaped pulses with durations down to 30 fs, at a repetition rate of 1 kHz and with 0.7 mJ energy per pulse. With this system most of the distortions accumulated by the laser pulse inside the regenerative amplification cavity can be compensated by a pulse shaper 53. At the same time, the loss introduced by the shaper is compensated at an amplifier 55. The result is a very stable source that achieves 30 fs pulse duration (33 nm bandwidth). Pulse shaper 53 is introduced between an oscillator 57 and regenerative amplifier 55 to compensate nonlinear phase distortions introduced by the laser system itself and farther down the beam path, and to compensate for spectral narrowing in the amplifier.

Figure 6:
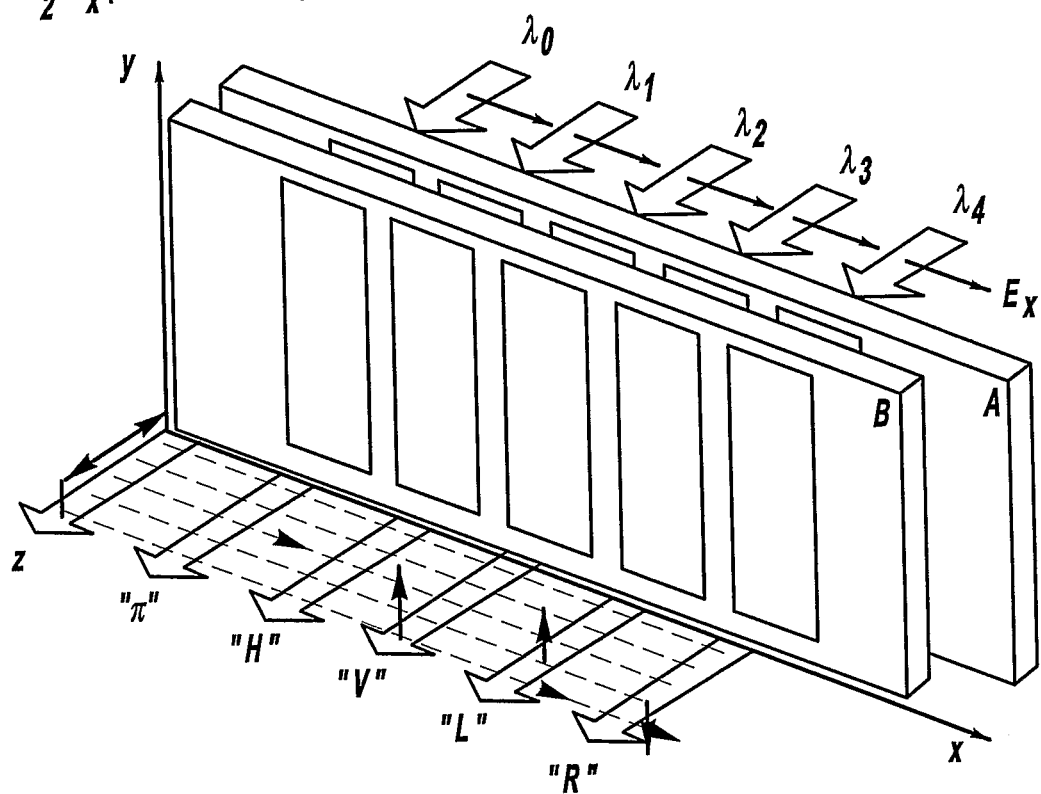
FIG. 6 shows a dual mask pulse shaper employed with the preferred embodiment laser system.

Another dimension of laser control employed with the present invention, beyond phase and amplitude, is control of the polarization state of the field. Full control of polarization requires four independent degrees of freedom for each spectral component. When using two orthogonally oriented liquid crystal spatial light modulators 71, as illustrated in FIG. 6, the incident x-polarized light ($E_x$) exits with field components ($E_x$, $E_y$) that depend on the phase retardance ($\phi_A$ and $\phi_B$) introduced by the liquid crystal elements whose slow axis is oriented at 45° and −45°. This arrangement together with an output polarizer can be used to achieve phase and amplitude shaping at each pixel. It is also possible with this arrangement to generate a linearly polarized output along the x ("H") or y ("V") axes or circular left ("L") or right ("R") polarized light $E'_L=(E_x-iE_y)/2^{0.5}$; $E'_R=(E_x+iE_y)/2^{0.5}$. Using a 5-bit basis set π, H, V, L, R (see FIG. 6 and Table 1), phase amplitude and polarization effects are produced very efficiently. This set does not cover all possible arbitrary fields, but provides a digital binary approach for electric field manipulation that, in most cases, is sufficient to explore the sensitivity of the system to the different properties of the field. Thus, it is possible to introduce a π phase delay for each pixel and rotate polarization horizontally or vertically, or to create right or left circular polarization.

Table 1, phase retardance for A and B elements to achieve binary states "0", $\phi_A^{(0)}$, $\phi_B^{(0)}$, and "1" $\phi_A^{(1)}$, $\phi_B^{(1)}$, in amplitude, phase, linear or circular polarization:

|  | Amplitude[a] (0, 1) | | Phase (0, π) | | Linear(H, V) | | Circular(L, R) | |
|---|---|---|---|---|---|---|---|---|
| "0" | $|E_x|^2 = 1$ | | $\phi = 0$ | | $E_x = 1$ | $E_y = 0$ | $E_L = 1$ | $E_R = 0$ |
| "1" | $|E_x|^2 = 0$ | | $\phi = \pi$ | | $E_x = 0$ | $E_y = 1$ | $E_L = 0$ | $E_R = 1$ |
| $\phi_A^{(0)}, \phi_B^{(0)}$ | 0 | 0 | 0 | 0 | 0 | | $\pi/4$ | $-\pi/4$ |
| $\phi_A^{(1)}, \phi_B^{(1)}$ | $\pi/2$ | $-\pi/2$ | $\pi/2$ | $\pi/2$ | 0 | $\pi$ | $-\pi/4$ | $\pi/4$ |

[a] An additional polarizer (x-oriented) is required at the output.

Rotation of the optical axis angle of the quarter-wave plate allows the operator to determine the ellipticity of polarization of the pulses. Circular polarizations are obtained at 45° and linear polarizations at 90°. Changing the optical axis angle provides a reliable control because it only affects the polarization of the beam but no other variable such as energy or dispersion. Occasionally, the femtosecond pulses are first linearly chirped in order to spread the different frequencies within the pulse in the time domain such that redder frequencies arrive first (positive chirp) or last (negative chirp).

The shaped and polarized femtosecond pulses of the present invention are preferably used to test for optically active or chiral characteristics of a specimen, more specifically for enantiomers and/or stereoisomers therein. In order to find the greatest enantiomeric specificity, the effect of 512 different circular-polarization shaped pulses are evaluated on the relative peak ratios of the different fragment ions of the samples. These pulses correspond to half of all possible 10-bit polarization functions that can be obtained by combining right- and left-circular polarization. From these 512 experiments, the pulses are found which give the greatest difference in ion product ratios (A/B) between the R- and S-enantiomers. From these pulses, mass spectra for both compounds are generated. The binary polarization that gives the greatest contrast between the compounds is automatically calculated and determined by controller 17. Using this polarization setting, a hundred measurements are made for each of the enantiomers.

In another theoretical example, this time with stretched laser pulses, it is expected that the pulses are a factor of two longer with the redder frequencies preceding the bluer ones or vice versa. Once again, one hundred measurements for each pulse type and molecule are employed; expected measured ratios between the fragments when circularly polarized negatively chirped pulses are used and then automatically evaluated by controller 17. The addition of negative or positive chirp may slightly increase the contrast ratio for the sample enantiomers. The contrast observed may be reversed when going from a negatively chirped pulse to one that is positively chirped. This reversal is predicted by the fact that the time order of the different frequency components of the pulse is reversed for positive or negative chirp.

By way of a theoretical example, a fragment ion corresponding to loss of a methyl group may exhibit the greatest sensitivity to the chiral laser pulses. Furthermore, the number of polarization flips introduced by the shaper correlates with the degree of contrast. This indicates that higher levels of discrimination will be possible using polarization phase functions with higher bit-resolution. Referring to FIGS. 3a and 3b, analysis of a number of electric fields that are found capable of enantiomeric resolution show a linear polarization component that precedes the large rotating component that is reminiscent to a propeller-like shape, in other words, with a helical and zig-zag radiating shape. The direction and curvature of the propeller component determines the enantio-selective photochemistry.

It is noteworthy that if the wave plate is rotated 45° then positive results are expected. But if it is rotated 0° or 90° then negative results are expected. Furthermore, pure left or right light is expected to generate negative results. All of the degrees are relative to the designed optical axis of the compound.

Two pulse shapers 33, 53 or 71 are provided so that the first one is controlled by the controller to correct phase distortions in the pulse and can impart both phase and amplitude shaping. The second shaper subsequently controls the final polarization of different frequency components in the shaped pulse. The pulse is preferably preceded by a long field of about 1-2 picoseconds that is plane polarized. This serves to align the molecular dipoles. Then, the shaped pulses should contain one or more propeller structures or characteristics to impart torques on the molecules. These torques break the molecules but enantiomers will twist in opposite directions. The propeller structures should have a duration between 20 fs and 1 ps to be effective on the molecular time scale. Such shaped pulses can be combined with a second linearly polarized laser that is also incident on the same molecules and aligns a second axis of the molecules. Accordingly, the molecules are aligned and oriented before the intense propeller pulse breaks the molecules. A final field is delayed in time and ionizes neutral fragments resulting from the interaction with the shaped pulses.

The present invention is used to test for chirality in the manufacture of pharmaceutical products. An electro-spray source is coupled to an ion trap mass spectrometer. Once the desired ions are trapped, the controller automatically interrogates them by the phase and polarization shaped pulses. This method advantageously interrogates ions such that the pulses only need to cleave one or more bonds but they do not have to ionize. This should increase enantiomer selectivity. Automated MIIPS pulse distortion detection and compensation in combination with polarization maximizes performance of the laser systems, especially for pharmaceutical manufacturing. Subsequent shaped pulses can then be automatically controlled by the controller to destroy undesired enantiomers in the product or compound.

Alternately, the present invention MIIPS shaping and polarization is employed in protein sequencing. This advantageously determines the handedness of the amino acids. The present invention should advantageously work even for very low concentrations in detecting and, optionally, destroying undesired amino acids with the incorrect chirality thereby removing poisons and diseases therein. In another variation, the present invention employs a circular dichroism spectrometer to determine a secondary protein structure of the specimen. The detected response of the specimen to differently shaped and/or polarized pulses provides information about the secondary structure of proteins and carbohydrates therein for analysis and/or determination by the controller.

It is noteworthy that the present invention's use of binary or 0/π settings of right and left polarization allows for testing of essentially all pulse shape values for enantiomer sensitivity testing, rather than prior experiments where only a limited quantity of shaping values were attempted since the genetic learning algorithms employed therein was overly time consuming. Thus, the system of the present invention preferably evaluates essentially all pulse shaping possibilities and then proceeds to carry out an exhaustive evaluation of the search space. The binary function reduces the search field in the present invention but without reducing effectiveness. This speeds up the analysis process considerably.

In summary, it is possible to prepare laser pulses capable of resolving enantiomeric pairs. At the fundamental level, the ability to prepare chiral pulses opens a window into the nature and dynamics of optical activity at the level of individual molecules. These observations can be developed for the reliable identification of a large number of enantiomeric species that would require analysis in areas such as metabolomics. A different application that could be envisioned would be the enantiomeric purification of a racemic mixture. Thus, enantiomeric identification and enhanced enantiomeric fragmentation of the present invention are ideally suited for testing chemical constituents for enantiomers for subsequent processing into pharmaceuticals. This type of laser pulse can also be used to determine the tertiary structure of proteins, for example beta-sheet or alpha-helix. It can also be used to identify enantiomeric characteristics in amino acid for use in protein sequencing. The pulse is automatically generated, shaped, chirped and polarized, then the pulse is used in a mass spectrometer, in combination with a controller, to automatically determine differences in fragmentation patterns, especially of enantiomers. Thereafter or simultaneously, the same pulse or a subsequent shaped and low intensity pulse can be used to either destroy undesired enantiomers (for example, left-handed molecules) in a mixed compound solution or to direct chemistry to prepare single-type enantiomers.

While various embodiments are disclosed, it is envisioned that further variations may fall within the scope of the present invention. For example, the pulse shaper may alternately provide 45° and/or circular polarization thereby negating the need for a separate quarter-wave plate. Furthermore, pulse durations of less than 1000 fs, less than 51 fs and possibly less than 10 fs may be used although some of the benefits of the present invention may not be realized. Similarly, the wavelength of the laser may be 800 nm, the fundamental wavelength of a titanium sapphire laser, its second harmonic may be at 400 nm or its third harmonic may be at 266 nm; such shorter second and/or third harmonic wavelengths may be advantageous for improved sensitivity in selective chemistry as compared to longer wavelengths which lead to field ionization and less sensitivity with molecular structures. For example, ultraviolet pulses of less than 100 fs may be used. Ultraviolet pulses having a center wavelength shorter than approximately 420 nm and a bandwidth greater than approximately 10 nm can be used with the present invention, especially with an actively controlled pulse shaper, and a pulse having a center wavelength less than 300 nm and a bandwidth greater than 5 nm is even more desirable. The present invention is also ideally suited for use in material processing, such as micromachining silicon microprocessor chips with a shaped and polarized laser pulse, especially employing MIIPS. While various materials and equipment types have been disclosed, it should be appreciated that a variety of other materials and hardware can be employed. It is intended by the following claims to cover these and any other departures from the disclosed embodiments which fall within the true spirit of this invention.

The invention claimed is:

1. A method of manufacturing a pharmaceutical compound, the method comprising:
    (a) emitting a laser beam;
    (b) shaping the laser beam with a shaper;
    (c) polarizing the laser beam;
    (d) testing the pharmaceutical compound with the shaped and polarized laser beam;
    (e) automatically determining a chiral property of the pharmaceutical compound based on the test;
    (f) creating a substantially helical and propeller-like direction and curvature of the polarized and shaped laser beam to cause enantiomeric selectivity; and
    (g) detecting a characteristic of the pharmaceutical compound with an ion trap mass spectrometer while interrogating ions in the pharmaceutical compound with phase and polarization shaped laser beam pulses.

2. The method of claim 1 further comprising emitting the laser beam with a pulse duration less than 100 femtoseconds.

3. The method of claim 1 further comprising polarizing the laser beam with a quarter-waveplate after the shaper.

4. The method of claim 1 further comprising electro-spraying the pharmaceutical compound.

5. The method of claim 1 further comprising cleaving bonds in the pharmaceutical compound with phase and polarization shaped laser beam pulses.

6. The method of claim 1 further comprising using multiphoton intrapulse phase scan to minimize distortions in the laser beam.

7. The method of claim 1 further comprising using at least two of: (a) zero, (b) π, (c) right, and (d) left, circular polarization to test for effectiveness in determining chiral sensitivity to different laser beam shapes.

8. The method of claim 1 further comprising:
    (a) correcting phase distortions of the laser beam with a first pulse shaper; and
    (b) polarizing the laser beam with the shaper which is a second pulse shaper, after the correcting step.

9. A method of manufacturing a pharmaceutical product, the method comprising:
    (a) emitting a set of laser beam pulses on the pharmaceutical product, each of the pulses having a duration of less than 100 femtoseconds;
    (b) shaping the pulses with a shaper to control phase and amplitude in the pulses;
    (c) automatically detecting and compensating for distortions in the pulses, without a genetic learning algorithm;
    (d) polarizing the pulses after step (b) to control the electric field direction therein;
    (e) detecting or changing a characteristic of the pharmaceutical product with the shaped and polarized pulses; and
    (f) detecting a characteristic of the pharmaceutical product with an ion trap mass spectrometer while interrogating ions in the pharmaceutical product with phase and polarization shaped laser beam pulses.

10. The method of claim 9 further comprising creating a substantially helical and propeller-like direction and curvature of the polarized and shaped laser beam pulses to cause enantiomeric selectivity.

11. The method of claim 9 further comprising polarizing the laser beam pulses with a quarter-wave plate after a shaper.

12. The method of claim 9 further comprising electro-spraying the pharmaceutical product.

13. The method of claim 9 further comprising cleaving bonds in the pharmaceutical product with phase and polarization shaped laser beam pulses.

14. The method of claim 9 further comprising using multiphoton intrapulse phase scan to minimize distortions in the laser beam pulses.

15. The method of claim 9 further comprising using at least two of: (a) zero, (b) π, (c) right, and (d) left, circular polarization to test for effectiveness in determining chiral sensitivity to different laser beam pulse shapes.

16. A method of operating a laser system, the method comprising:
   (a) emitting a laser beam pulse on a pharmaceutical compound;
   (b) minimizing phase distortions of the pulse by pulse shaping without a genetic learning algorithm;
   (c) polarization shaping of the pulse after step (b); and
   (d) detecting a characteristic of a pharmaceutical compound with an ion trap mass spectrometer while interrogating ions in the pharmaceutical compound with phase and polarization shaped laser beam pulses.

17. The method of claim 16 further comprising creating a substantially helical and propeller-like direction and curvature of the polarized and shaped laser beam to cause enantiomeric selectivity.

18. The method of claim 16 further comprising:
   (a) emitting the pulse with a duration of less than 51 femtoseconds; and
   (b) minimizing phase distortions in an iterative manner using a series of laser beam pulses.

19. The method of claim 16 further comprising cleaving bonds in a pharmaceutical compound with phase and polarization shaped laser beam pulses.

20. The method of claim 16 further comprising automatically destroying undesired enantiomers with the pulse.

21. The method of claim 16 further comprising electrospraying the pharmaceutical compound.

22. The method of claim 16 further comprising using multiphoton intrapulse phase scan to minimize distortions in the laser beam pulse.

23. The method of claim 16 further comprising:
   (a) correcting phase distortions of the laser beam pulse with a first pulse shaper; and
   (b) polarizing the laser beam pulse with a second pulse shaper after the correcting step.

24. The method of claim 16 further comprising using vertical linear, horizontal linear, right circular and left circular pulse shapes for the determining chiral sensitivity.

25. The method of claim 16 further comprising changing a characteristic of the pharmaceutical compound with the shaped and polarized pulse.

26. The method of claim 16 further comprising detecting a chiral characteristic of the pharmaceutical compound with the shaped and polarized pulse.

27. The method of claim 16 further comprising using a programmable controller to automatically cause a polarizer to vary the polarization based at least in part on a signal from the spectrometer, without a genetic learning algorithm.

* * * * *